United States Patent
Mills et al.

(10) Patent No.: US 11,497,805 B2
(45) Date of Patent: Nov. 15, 2022

(54) TOLL-LIKE RECEPTOR 2 AGONISTS AND VACCINES AND USES THEREOF

(71) Applicant: The Provost, Fellows, Foundation Scholars & the Other Members of Board, of the College of the Holy & Undivided Trinity of Queen Elizabeth, Near Dublin, Dublin (IE)

(72) Inventors: Kingston Mills, Dublin (IE); Aisling Dunne, Dublin (IE)

(73) Assignee: The Provost, Fellows, Foundation Scholars & the Other Members of Board, of the College of the Holy & Undivided Trinity of Queen Elizabeth, Near Dublin, Dublin (IE)

( * ) Notice: Subject to any disclaimer, the term of this patent is extended or adjusted under 35 U.S.C. 154(b) by 135 days.

(21) Appl. No.: 16/271,802

(22) Filed: Feb. 9, 2019

(65) Prior Publication Data

US 2019/0224296 A1    Jul. 25, 2019

Related U.S. Application Data

(62) Division of application No. 15/126,069, filed as application No. PCT/EP2015/055735 on Mar. 18, 2015, now abandoned.

(30) Foreign Application Priority Data

Mar. 19, 2014 (EP) .................................... 14160791

(51) Int. Cl.
*A61K 39/02* (2006.01)
*A61K 39/39* (2006.01)
*C07K 14/705* (2006.01)
*A61K 39/00* (2006.01)

(52) U.S. Cl.
CPC ............ *A61K 39/099* (2013.01); *A61K 39/39* (2013.01); *C07K 14/705* (2013.01); *A61K 2039/55511* (2013.01); *A61K 2039/55516* (2013.01); *A61K 2039/57* (2013.01); *A61K 2039/572* (2013.01); *A61K 2039/585* (2013.01); *A61K 2039/6018* (2013.01)

(58) Field of Classification Search
None
See application file for complete search history.

(56) References Cited

U.S. PATENT DOCUMENTS

2007/0116711 A1* 5/2007 Castado ............... A61K 39/099
                                                        424/190.1
2011/0294736 A1* 12/2011 Mills .................... A61P 37/02
                                                        514/13.2

FOREIGN PATENT DOCUMENTS

WO   WO-03051305 A2    6/2003
WO   WO-2005032584 A2  4/2005
WO   WO-2005077408 A2  8/2005

OTHER PUBLICATIONS

Parkhill, J., et al., Nature Genetics, 2003, vol. 35, pp. 32-40. (Year: 2003).*
Ross et al. PLOS Pathogens vol. 9, issue 4 pp. 1-14, Apr. 2013 . (Year: 2013).*
Higgs, R., et al., "Immunity to the Respiratory Pathogen *Bordetella pertussis*," Mucosal Immunol., Jun. 20, 2012, pp. 485-500.
Lee, H.K., et al., "Two Lipoproteins Extracted From *Escherichia coli* K-12 LCD25 Lipopolysaccharide Are the Major Components Responsible for Toll-Like Receptor 2-Mediated Signaling," The Journal of Immunology, Apr. 15, 2002, vol. 168, No. 8, pp. 4012-4017.
Sha, J., et al., "The Two Murein Lipoproteins of *Salmonella enterica* Serovar Typhimurium Contribute to the Virulence of the Organism," Infection and Immunity, Jul. 2004, vol. 72, No. 7, pp. 3987-4003.
Dunne, A., et al., "A Novel TLR2 Agonist From *Bordetella pertussis* Is a Potent Adjuvant That Promotes Protective Immunity With an Acellular Pertussis Vaccine," Mucosal Immunology, Oct. 15, 2014, pp. 1-11.
Database UniProt [Online], Jan. 9, 2013 (Jan. 9, 2013), "Subname: Full-Putative lipoprotein {ECO:0000313|EMBL:CCN22419.1};", XP002732956, retrieved from EBI accession No. UNIPROT:K4TQM3, Database accession No. K4TQM3 sequence.
Database UniProt [Online], Jan. 9, 2013 (Jan. 9, 2013), "Subname: Full=Putative lipoprotein {ECO:0000313|EMBL:CCJ55029.1};", XP002732957, retrieved from EBI accession No. UNIPROT:K4QGF6, Database accession No. K4QGF6 sequence.
Database UniProt [Online], Jan. 9, 2013 (Jan. 9, 2013), "Subname: Full=Uncharacterized protein {ECO:0000313|EMBL:CCJ55900.1};", XP002732958, retrieved from EBI accession No. UNIPROT:K4QPT6, Database accession No. K4QPT6 sequence.
Database UniProt [Online], Oct. 1, 2003 (Oct. 1, 2003), "Subname: Full=Putative lipoprotein {ECO:0000313|EMBL:CAE41858.1};", XP002739309, retrieved from EBI accession No. UNIPROT:Q7VXZ9, Database accession No. Q7VXZ9, sequence.
Dillon, Stephanie, et al.; "Yeast Zymosan, a Stimulus for TLR2 and Dectin-1, Induces Regulatory Antigen-Presenting Cells and Immunological Tolerance"; The Journal of Clinical Investigation, vol. 116, No. 4; Apr. 2006; pp. 916-928.
Dunne, Aisling, et al.; "Inflammasome Activation by Adenylate Cyclase Toxin Directs Th17 Responses and Protection against *Bordetella pertussis*"; The Journal of Immunology, vol. 185; Jul. 7, 2010; pp. 1711-1719.

(Continued)

*Primary Examiner* — Jana A Hines
*Assistant Examiner* — Khatol S Shahnan Shah
(74) *Attorney, Agent, or Firm* — Winstead PC

(57) ABSTRACT

The present invention relates to Toll-Like Receptor 2 (TLR2) agonists, in particular, to TLR2-activating lipoproteins, and more particularly to TLR2-activating lipopeptides derived from the bacteria *Bordetella pertussis*. The invention further extends to the use of said

(56) References Cited

OTHER PUBLICATIONS

Higgins, Sarah C., et al.; "Toll-Like Receptor 4-Mediated Innate IL-10 Activates Antigen-Specific Regulatory T Cells and Confers Resistance to *Bordetella pertussis* by Inhibiting Inflammatory Pathology"; The Journal of Immunology, vol. 171; Sep. 15, 2003; pp. 3119-3127.
Ross, Pádraig J., et al.; "Relative Contribution of Th1 and Th17 Cells in Adaptive Immunity to *Bordetella pertussis*: Towards the Rational Design of an Improved Acellular Pertussis Vaccine"; PLoS Pathog 9(4); Apr. 4, 2013; 14 pages.
Sutherland, Jamie N., et al.; "Antibodies Recognizing Protective Pertussis Toxin Epitopes are Preferentially Elicited by Natural Infection versus Acellular Immunization"; Clinical and Vaccine Immunology, vol. 18, No. 6; Jun. 2011; pp. 954-962.
Ansel, Howard C., et al.; "Ansel's Pharmaceutical Dosage Forms and Drug Delivery Systems"; Ninth Edition; Lippincott Williams & Wilkins; Jan. 2010; 722 pages.
Parkhill, J., et al., "Comparative analysis of the genome sequences of Bordetella pertussis, Bordetella parapertussis and Bordetella bronchiseptica," Nature Genetics, 2003, vol. 35, pp. 32-40.

\* cited by examiner

BP1569 (SEQ ID NO:1)
MRMN<u>KR</u>HAGASALMALAL<u>LAGC</u>SDVNQLLGNEESVDYKSTRRGDPLSIPPDLTQANNDP
RYKAPASGTATYSQFQQQGLQQQASAGQNTNVLPERADMRVERDGDLRWLVIERPPEQLF
SKVVDFWTDTGFTVSVNNPQAGHETDWAENRAKIPESWLRQVLGSVLETAWDSGEREKF
RTRVERVNGHTEIYITHNQMLEKRVGSDGGQVQWTHGKEDPGLNAAMLARLMVYLGTDV
DAARKLVAQAEAAPQAPKVQSVRAEGAMLVVDESFDRAWRRVGVALDSGGFAVDDRDRS
AGEYFVRYVDTDTGAQNEQPGFFSRLFSSDKKAQAPQYRIRLTGSGTQTQVTVLDANGQRD
SSATAQRMLSVLKDKMV

BP2992 (SEQ ID NO:2)
MNYMHSPSVVAG<u>RARR</u>LLAVAAVAGSVAV<u>LAGC</u>ANPSASSGVYTYGQAQREQIVRTGTVTG
VRPITIQNDKSSGVGLVAGGALGGVAGNAVGGGTGRTIATVGGVILGALAGNAIENRAGKSSG
YEITVRLDNGETRVVAQEADVPISVGQRVQVISGAGPTRVTPY

BP0205 (SEQ ID NO:3 )
MQLTIRKLAYTLAFSTLVLAG<u>C</u>TTASKKTDGQAATPADQASSQQASAASVEFYVAQAKAGD
GLMEVKVPDGSLYMQRQPVLTRADLTEAAALVDRQGQNFVGLRFTEAGARKLNDISSKNIG
NMLALVIDRELVAAPRIAEPLNRGVLAFGVPSAKAASEIAAKIRGDAGAPAAGVPAAPAPKP
APKP

BP3342 (SEQ ID NO:4 )
MKSRIAKSLTIAALAATLAA<u>C</u>SSVPLDDKAGQAGGSGQGSASGQILDPFNPQSILAQQRSVY
FDFDSYTVSEQYRGLVETHARYLASNNQQRIKIEGNTDERGGAEYNLALGQRRADAVRRM
MTLLGVSDNQIETISFGKEKPKATGSSEADFAENRRADIVYQR

BP3819 (SEQ ID NO:5)
MSAPLDTPALRLNTRFATGIVLAGTLALAG<u>C</u>AQQRSAGYYDPPGASTITDAQYQGQAAGYR
TVVHAPSQLQIELKPNQPARQQNAQAQAGQQSTEDGTAVPEGQAAPQPQPETASPGAQAII
PQAQTYQGTFPCFAAGLACEAQRVTLTLAPNGRWRSRTNYLDKQPQASAPVAEQGCWDAT
QERPPRVLLLDGSGNMRAELVMTANNVLRVRSVGGRTPNLNYNLTRQPDLDAIAELDKQA
APKCP

BP2508 (SEQ ID NO:6 )
MIARISLRPLKGLAVAVLAASALTA<u>C</u>SSGKWGFPYKAGVQQGNWITKEQVALLQQGMSREQ
VRFALGSPTLTSVLHADRWDYPYYFKPGYGKAQERQFTVWFENDHLVRWSGDEQPDLQP
FQIEKVNAKQEEKADAQVDTAEKRQEGIDKAEKVRPHVDVTTPDNPTLDYPGEPGQTFEP
LK

FIGURE 1A

| Name | N-terminal Signal peptide: |
|---|---|
| LP0205 | MQLTIR K LAYTLAFSTLV LAG<u>C</u> (SEQ ID NO:9) |
| LP1569 | MRMNK R HAGASALMALAL LAG<u>C</u> (SEQ ID NO:7) |
| LP3342 | MKSRIA K SLTIAALAAT LAA<u>C</u> (SEQ ID NO:10) |
| LP3819 | MSAPLDTPALRLNTRFATGIVLAGTLA LAG<u>C</u> (SEQ ID NO:11) |
| LP2508 | MIARISLRPL K GLAVAVLAASA LTA<u>C</u> (SEQ ID NO:12) |
| LP2992 | MNYMHSPSVVAGRARRLLAVAAVAGSVAV LAG<u>C</u> (SEQ ID NO:8) |

FIGURE 1B

Lipopeptide 1569
CSDVNQLLGNEESVD (SEQ ID NO:13)

Lipopeptide 2992
CANPSASSGVYTYGQ (SEQ ID NO:14)

FIGURE 1C

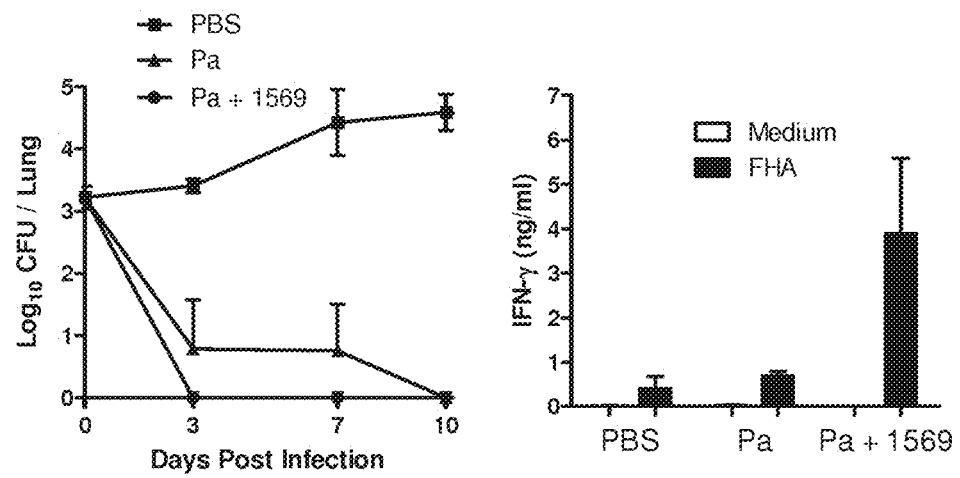
FIGURE 8A
FIGURE 8C
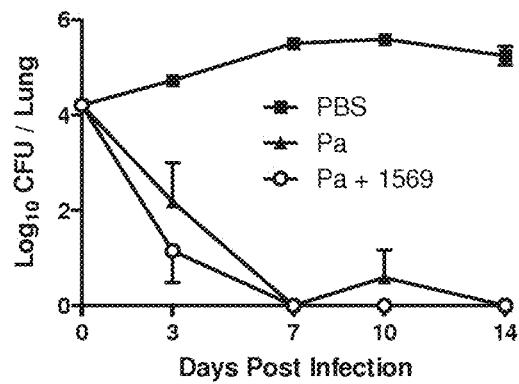
FIGURE 8B

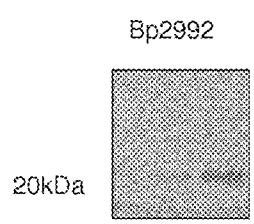
FIGURE 9A
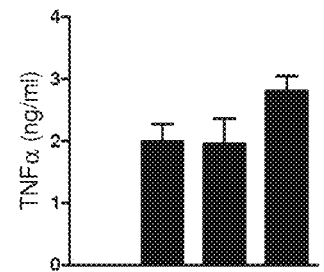
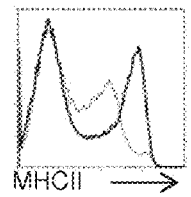
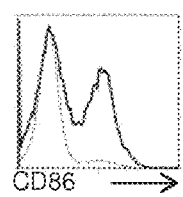
FIGURE 9C
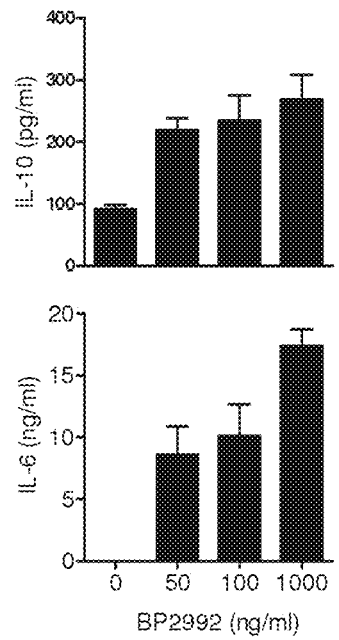
FIGURE 9B

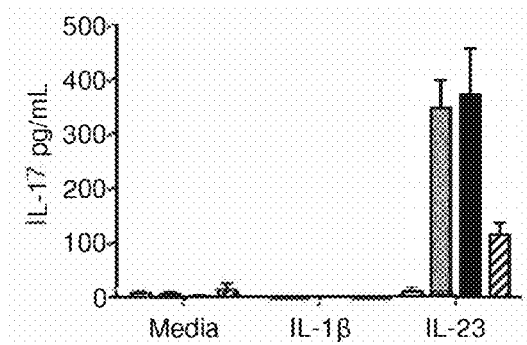
FIGURE 12A1
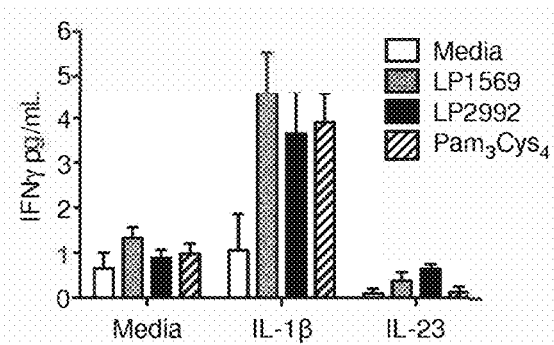
FIGURE 12A2
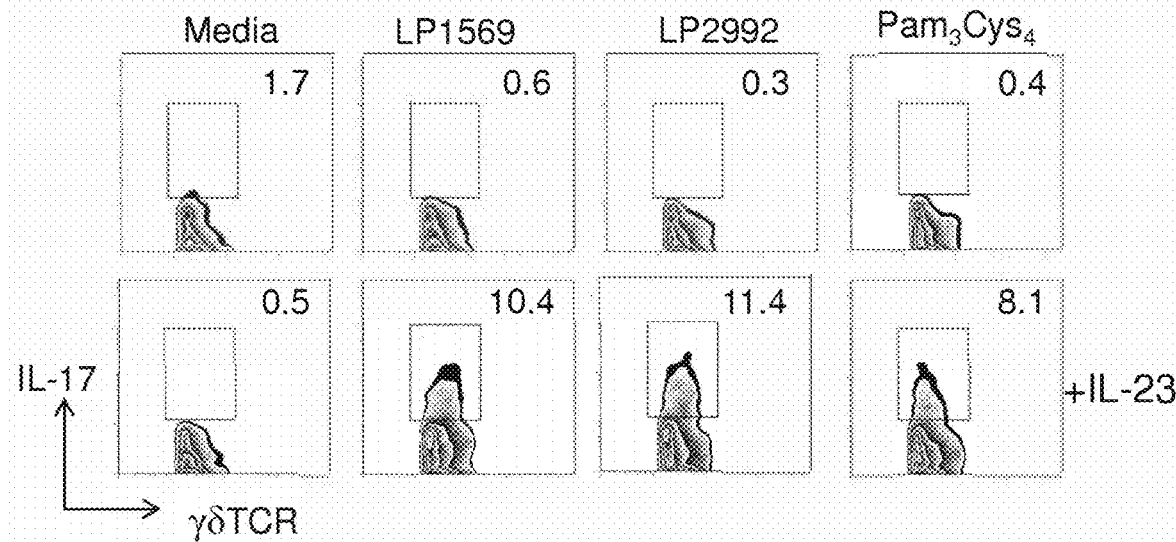
FIGURE 12B

TOLL-LIKE RECEPTOR 2 AGONISTS AND VACCINES AND USES THEREOF

CROSS-REFERENCE TO RELATED APPLICATIONS

This application is a divisional of U.S. patent application Ser. No. 15/126,069, filed on Sep. 14, 2016. U.S. patent application Ser. No. 15/126,069 claims priority to PCT/EP2015/055735 filed on Mar. 18, 2015, which claims priority to EP14160791.1 filed Mar. 19, 2014. U.S. patent application Ser. No. 15/126,069, Application No. PCT/EP2015/055735, and Application No. EP14160791.1 are incorporated herein by reference in their entirety.

FIELD OF THE INVENTION

The present invention relates to Toll-Like Receptor 2 (TLR2) agonists, in particular, to TLR2-activating lipoproteins, and more particularly to TLR2-activating lipopeptides derived from the bacteria *Bordetella pertussis*. The invention further extends to the use of said TLR2-activating lipoproteins as a therapeutic or as part of a vaccine composition in the treatment and prevention of infectious diseases, cancer or allergic diseases.

BACKGROUND TO THE INVENTION

The bacterium *Bordetella pertussis* is the causative agent of whooping cough, a severe and debilitating respiratory tract infection affecting infants and young children. Whooping cough (pertussis) still accounts for over 300,000 infant deaths annually, mostly in developing countries. The disease was largely controlled in developed countries through vaccination with whole cell pertussis vaccines (Pw), which were introduced in the 1950s. However, these vaccines were associated with unacceptable side effects and were replaced in many countries in the 1990s by acellular pertussis vaccines (Pa), composed of individual *B. pertussis* antigens absorbed to alum as the adjuvant. More recently, studies in children and mice have demonstrated that Pa promote the induction of Th2 and Th17 cells and this has been attributed to the use of alum as the adjuvant. In contrast, Pw induce Th1 and Th17 responses and confer a higher level of protection against infection in mice and in children and this is thought to reflect the presence of *B. pertussis*-derived pathogen associated molecular patterns (PAMPs), including agonists for Toll-like receptors (TLRs) (Higgs et al).

Th1 cells are characterized by the production of pro-inflammatory cytokines such as IFN-γ, IL-2, and TNF-β. Th1 cells are involved in cell-mediated immunity (CMI), this being the immune response typically mounted against viruses and intracellular pathogens.

Th17 cells secrete IL-17 and are involved in immune responses to infection and tumours. Functionally, Th17 cells play a role in host defence against extracellular pathogens by mediating the recruitment of neutrophils and macrophages to infected tissues. They are, therefore, largely part of the cellular immune response together with Th1 cells. The IL-17 cytokine family is a group of cytokines including IL-17A, B, C, D, IL-17E (IL-25) and IL-17F. It is increasingly recognized that besides T cells, other cells such as NK cells and neutrophils might also be an important source of IL-17. Besides IL-17A, the major cytokine produced by Th17 cells, these cells also release IL-17F, IL-21 and IL-22.

Toll-like Receptors (TLRs) are part of a family of pattern recognition receptors (PRRs) which have evolved for innate immune recognition of conserved microbial products. TLRs have a key role in modulating the innate immune response; they are also involved in tissue repair, maintenance of tissue integrity and tumorigenesis. Eleven Toll-like Receptors have been identified in humans to date. The binding of pattern-associated molecular patterns (PAMPs), such as TLR ligands to pathogen recognition receptors on cells of the innate immune system, such as macrophages and dendritic cells (DCs), activates signalling pathways leading to pro-inflammatory gene expression and the induction of innate immune responses. This in turn helps to drive adaptive immunity. Consequently TLR agonists have been exploited commercially as adjuvants in vaccines to boost immune responses to antigens and as direct immunotherapeutics for cancer. The members of the TLR family are highly conserved, with most mammalian species having between 10 to 15 Toll-like Receptors. Toll-like Receptor 2 (TLR2, CD282, TLR-2) can be activated by peptidoglycan, lipoproteins, lipoteichoic acid and endogenous ligands. Lipoproteins are biochemical assemblies comprising both proteins and lipids. The consensus view is that TLR2 activation is more anti-inflammatory than other TLRs; for example it has been reported that TLR2 induced regulatory antigen presenting cells and immunological tolerance (Dillon et al).

Although the number of cases of pertussis continued to decline following introduction of acellular pertussis vaccines (Pa), in recent years there has been alarming increases in the incidence of disease not only in infants but also in adolescents and young adults. This has been attributed to antigenic variation in protective antigens or waning and ineffective immunity induced with current Pa. The resurgence in pertussis has consequently called into question the level of protection provided by current vaccines and highlighted the need for a better vaccine.

SUMMARY OF THE INVENTION

The inventors of the present invention have surprisingly discovered that novel Toll-like Receptor 2 lipoprotein ligands from *B. pertussis* are capable of activating innate inflammatory immune responses that drive the induction of protective adaptive cellular immunity to *B. pertussis*. The present inventors have identified lipopeptides that enhance Th1 and Th17 responses and in particular provide more effective and longer lasting protective immunity to *B. pertussis.*

Following extensive experimentation, the present inventors have identified and characterised novel TLR2-activating lipopeptides derived from *B. pertussis*. The present inventors have demonstrated that these novel lipopeptidess specifically activate TLR2 and surprisingly drive potent pro-inflammatory cytokine production. Furthermore, the inventors have demonstrated that corresponding synthetic lipopeptides have potent adjuvant properties, promoting protective Th1 and Th17 responses against *B. pertussis* infection in vivo when co-administered with pertussis antigens. These findings demonstrate that combining protective antigens with an adjuvant based on an endogenous TLR2 ligand from *B. pertussis* has considerable potential for the development of a more effective vaccine capable of generating protective cellular immunity against pathogens and in generating Th1/Th17 immune responses in relation to other conditions such as cancer or allergic diseases and in particular against the re-emerging *B. pertussis* pathogen.

According to a first aspect of the present invention, there is provided at least one lipoprotein obtainable from *Bordetella pertussis* (*B. pertussis*) for enhancing a Th1 response, the lipoprotein having an N terminal signal peptide of less than 40 amino acids in length wherein the N terminal signal peptide comprises a lipobox comprising an amino acid sequence X1, X2, X3, X4, wherein X1 can be selected from Leucine, Valine and Isoleucine; X2 can be selected from Alanine, Serine, Threonine, Valine and Isoleucine; X3 can be selected from Glycine, Alanine, and Serine; and X4 is Cysteine, wherein X4 is capable of being acylated, or a fragment or derivative thereof wherein the lipoprotein or the fragment or derivative thereof is a Toll-like receptor 2 (TLR-2) agonist As will be understood by those of skill in the art, whilst the lipoproteins of the present invention were identified from *Bordetella pertussis*, such lipoproteins or a fragment or derivative thereof may also be obtained by synthetic routes.

Suitably, a lipoprotein or a fragment or derivative thereof may be obtained from *B. pertussis*.

Suitably a lipoprotein or a fragment or derivative thereof may be obtained from a soluble secreted fraction of the *B. pertussis*.

In embodiments a lipoprotein of the present invention can comprise an amino acid sequence selected from SEQ ID NO:1, SEQ ID NO:2, SEQ ID NO:3, SEQ ID NO:4, SEQ ID NO:5, and SEQ ID NO:6 or can be a derivative or fragment thereof.

In embodiments a lipoprotein of the present invention can comprise or consist of an amino acid sequence selected from SEQ ID NO:1, SEQ ID NO:2, SEQ ID NO:3, SEQ ID NO:4, SEQ ID NO:5, and SEQ ID NO:6 or can be a derivative or fragment thereof.

In embodiments, a lipoprotein of the invention or a fragment, or derivative thereof can promote a Th1 response and/or a Th17 response or suppress a Th2 response against a pathogen, cancer or an allergic disease.

In embodiments a derivative can be a Toll-like receptor 2 (TLR-2) agonist lipoprotein of SEQ ID NO:1, SEQ ID NO:2, SEQ ID NO:3, SEQ ID NO:4, SEQ ID NO:5, and SEQ ID NO:6 from a gram negative bacterium which is not *B. pertussis*.

In embodiments a derivative of a lipoprotein of the first aspect of the invention can be a lipopeptide comprising an exposed acyl coupled N-terminus. Suitably the exposed acyl coupled N-terminus may be formed from cleavage of a lipoprotein of the invention between X3 and X4 of the lipobox comprising an amino acid sequence X1, X2, X3, X4, wherein X1 can be selected from Leucine, Valine and Isoleucine; X2 can be selected from Alanine, Serine, Threonine, Valine and Isoleucine; X3 can be selected from Glycine, Alanine, and Serine; and X4 is Cysteine.

In embodiments a derivative or fragment of a lipoprotein of the first aspect of the invention can be from the soluble fraction from *B. Pertussis*. In alternative embodiments, a derivative or fragment of a lipoprotein of the first aspect of the invention can be synthetically or recombinantly produced.

In embodiments a fragment of a lipoprotein of the first aspect of the invention can be a lipopeptide fragment selected from SEQ ID NO: 13 or SEQ ID NO: 14.

```
(Lipopeptide 1569)
                                    SEQ ID NO: 13
CSDVNQLLGNEESVD (Lipopeptide 2992)
                                    SEQ ID NO: 14
CANPSASSGVYTYGQ
```

In embodiments, a lipopeptide comprising or consisting of SEQ ID NO: 13 or SEQ ID NO: 14 comprises an exposed acyl coupled N-terminus, for example a diacylated or triacylated N-terminal cysteine, in particular the cysteine can be palmitoylated.

A fragment can comprise at least 10, suitably 20, 50, suitably 100 and suitably 150 or greater contiguous amino acids from the relevant sequence and which is functionally active.

A derivative can comprise an amino acid sequence which is at least 70% homologous to the relevant sequence, more preferably at least 80% homologous, more preferably at least 90% homologous, even more preferably at least 95% homologous, more preferably at least 97%, most preferably at least 99% homologous. A derivative encompasses a polypeptide sequence of SEQ ID NO: 1 which includes substitution of amino acids, especially a substitution(s) which is/are known for having a high probability of not leading to any significant modification of the biological activity or configuration, or folding, of the protein. These substitutions, typically known as conserved substitutions, are known in the art. For example the group of arginine, lysine and histidine are known interchangeable basic amino acids. Suitably, in embodiments amino acids of the same charge, size or hydrophobicity may be substituted with each other. Suitably, any substitution may be selected based on analysis of amino acid sequence alignments of lipoproteins to provide amino acid substitutions to amino acids which are present in other lipoproteins at similar or identical positions when the sequences are aligned. Hybrids, and derivatives and fragments thereof may be generated using suitable molecular biology methods as known in the art.

Suitably, the N-terminal signal peptide including the lipobox further comprises a region of positively charged amino acids and a region of hydrophobic amino acids. Suitably, the N-terminal signal peptide can thus comprise the structure, a region of positively charged amino acids towards the N-terminus of the N-terminal signal peptide, a lipobox at the C-terminus of the N-terminal signal peptide and a, region of hydrophobic amino acids interposed between the positively charged amino acid region and the lipobox.

By positively charged region it is meant about 5-7 residues, comprising at least 2 positively charged amino acid residues, for example Lys or Arg residues. By hydrophobic region it is meant an intervening stretch of uncharged amino acid residues, for example phenylalanine, leucine, alanine, isoleucine, valine, methionine, tryptophan, proline, between the positively charged region and the lipobox. Typically the positively charged region and hydrophobic region can span 7-22 amino acids in length. By lipobox, it is meant a distinct sequence at the C-terminal end of the signal peptide. The lipobox contains the invariant Cys that is lipid-modified.

In embodiments, the at least one TLR2-activating lipoprotein or lipopeptide can be obtained from the bacteria *Bordetella pertussis*.

In embodiments, the at least one TLR2-activating lipoprotein or lipopeptide can be provided by recombinant means.

In embodiments, the exposed acyl of a lipopeptide of the invention can be a diacylated group or a triacylated group and preferably a triacylated group.

Suitably, a lipoprotein or fragment or derivative thereof enhances a Th1 response against a pathogen or cancer or in an allergic disease or condition.

Suitably a pathogen may be any infectious agent, in particular a bacterium, a virus, a fungus or a parasite.

In certain embodiments, the pathogen can be *B. pertussis*.

In embodiments, cancer can be hepatic cancer, lung cancer, in particular non-small cell lung cancer, prostate cancer, ovarian cancer, breast cancer, melanoma, basal cell carcinoma, or haematological malignancies.

In certain embodiments, the allergic disease can be asthma.

In certain embodiments, a TLR2-activating lipopeptide can be a fragment of a lipoprotein comprising the amino acid sequence of SEQ ID NO:1 or SEQ ID NO:2.

SEQ ID NO:1 is the full length sequence of *B. pertussis* lipoprotein BP1569; SEQ ID NO:2 is the full length sequence of *B. pertussis* lipoprotein BP2992; SEQ ID NO:3 is the full length sequence of *B. pertussis* lipoprotein BP0205; SEQ ID NO:4 is the full length sequence of *B. pertussis* lipoprotein BP3342; SEQ ID NO:5 is the full length sequence of *B. pertussis* lipoprotein BP3819 and SEQ ID NO:6 is the full length sequence of *B. pertussis* lipoprotein BP2508.

In the below sequences positively charged residues and putative lipobox are highlighted in bold and the invariant cysteine residue is underlined.

(BP1569)
SEQ ID NO: 1
MRMNKRHAGASALMALALLAGCSDVNQLLGNEESVDYKSTRRGDPLSIPP

DLTQANNDPRYKAPASGTATYSQFQQQGLQQQASAGQNTNVLPERADMRV

ERDGDLRWLVIERPPEQLFSKVVDFWTDTGFTVSVNNPQAGIIETDWAEN

RAKIPESWLRQVLGSVLETAWDSGEREKFRTRVERVNGHTEIYITHNQML

EKRVGSDGGQVQWTHGKEDPGLNAAMLARLMVYLGTDVDAARKLVAQAEA

APQAPKVQSVRAEGAMLVVDESFDRAWRRVGVALDSGGFAVDDRDRSAGE

YFVRYVDTDTGAQNEQPGFFSRLFSSDKKAQAPQYRIRLTGSGTQTQVTV

LDANGQRDSSATAQRMLSVLKDKMV (BP2992)
SEQ ID NO: 2
NYMHSPSVVAGRARRLLAVAAVAGSVAVLAGCANPSASSGVYTYGQAQRE

QIVRTGTVTGVRPITIQNDKSSGVGLVAGGALGGVAGNAVGGGTGRTIAT

VGGVILGALAGNAIENRAGKSSGYEITVRLDNGETRVVAQEADVPISVGQ

RVQVISGAGPTRVTPY (BP0205)
SEQ ID NO: 3
MQLTIRKLAYTLAFSTLVLAG<u>C</u>TTASKKTDGQAATPADQASSQQASAASV

EFYVAQAKAGDGLMEVKVPDGSLYMQRQPVLTRADLTEAAALVDRQGQNF

VGLRFTEAGARKLNDISSKNIGNMLALVIDRELVAAPRIAEPLNRGVLAF

GVPSAKAASEIAAKIRGDAGAPAAGVPAAPAPKPAPKP (BP3342)
SEQ ID NO: 4
MKSRIAKSLTIAALAATLAA<u>C</u>SSVPLDDKAGQAGGSGQGSASGQILDPFN

PQSILAQQRSVYFDFDSYTVSEQYRGLVETHARYLASNNQQRIKIEGNTD

ERGGAEYNLALGQRRADAVRRMMTLLGVSDNQIETISFGKEKPKATGSSE

ADFAENRRADIVYQR (BP3819)
SEQ ID NO: 5
MSAPLDTPALRLNTRFATGIVLAGTLALAG<u>C</u>AQQRSAGYYDPPGASTITD

AQYQGQAAGYRTVVHAPSQLQIELKPNQPARQQNAQAQAGQQSTEDGTAV

PEGQAAPQPQPETASPGAQAIIPQAQTYQGTFPCFAAGLACEAQRVTLTL

APNGRWRSRTNYLDKQPQASAPVAEQGCWDATQERPPRVLLLDGSGNMRA

ELVMTANNVLRVRSVGGRTPNLNYNLTRQPDLDAIAELDKQAAPKCP (BP2508)
SEQ ID NO: 6
MIARISLRPLKGLAVAVLAASALTA<u>C</u>SSGKWGFPYKAGVQQGNWITKEQV

ALLQQGMSREQVRFALGSPTLTSVLHADRWDYPYYFKPGYGKAQERQFTV

WFENDHLVRWSGDEQPDLQPFQIEKVNAKQEEKADAQVDTAEKRQEGIDK

AEKVRPHVDVTTPDNPTLDYPGEPGQTFEPLK

Without wishing to be bound by theory, the inventors submit that the lipoproteins identified in the present invention contain a unique N-terminal signal peptide characteristic of bacterial lipoproteins from Gram negative bacteria. In embodiments, the lipoproteins of the present invention can be triacylated with palmytic acid or can be a diacylated lipid.

According to a second aspect of the present invention there is provided a method for the simultaneous, separate or sequential administration of at least one TLR2-activating lipoprotein, or fragment or derivative thereof, for example a lipopeptide comprising the amino acid sequence of SEQ ID NO:13 or SEQ ID NO:14 as part of a vaccine composition for the treatment of or prophylaxis of a condition caused by a pathogen or tumourigenesis. In certain embodiments, the at least one TLR2-activating lipoprotein, or fragment or derivative thereof, for example a lipopeptide comprising the amino acid sequence of SEQ ID NO:13 or SEQ ID NO:14 is an adjuvant. In certain embodiments, the pathogen is the bacteria *B. pertussis*. In certain embodiments, the vaccine composition comprises at least one antigen derived from an infectious disease or a tumour for example a tumour specific or tumour-associated antigen. In certain embodiments, the at least one antigen is derived from *B. pertussis*. In certain embodiments, the vaccine composition comprises an allergen.

According to a further aspect of the present invention, there is provided a composition to mediate an immune response in a subject the composition comprising the at least one TLR2-activating lipoprotein, or fragment or derivative thereof of the present invention, for example a lipopeptide comprising the amino acid sequence of SEQ ID NO:13 or SEQ ID NO:14. In embodiments, the lipoprotein, or fragment or derivative thereof, for example the lipopeptide comprising the amino acid sequence of SEQ ID NO:13 or SEQ ID NO:14 is an immunogenic determinant in such a composition. In embodiments, the lipoprotein, or fragment or derivative thereof, for example the lipopeptide comprising the amino acid sequence of SEQ ID NO:13 or SEQ ID NO:14 can provide adjuvant activity in such a composition.

In certain embodiments, the lipoprotein, or fragment or derivative thereof of the present invention, for example compositions comprising a lipopeptide comprising the amino acid sequence of SEQ ID NO:13 or SEQ ID NO:14 are for use in mediating an immune response against a pathogen, against tumour cells or against an allergen. Said lipoprotein, or fragment or derivative thereof, for example vaccine compositions including the lipoprotein, or fragment or derivative thereof, are typically administered to mammals, in particular humans, in order to confer protective immunity against the pathogen/infectious agent.

In certain embodiments, the composition comprises the at least one TLR2-activating lipoprotein, or fragment or derivative thereof, for example a lipopeptide comprising the amino acid sequence of SEQ ID NO:13 or SEQ ID NO:14 as the adjuvant. In certain embodiments the vaccine or vaccine composition comprises the at least one TLR2-activating lipoprotein, or fragment or derivative thereof, for example lipopeptide as the antigen.

In embodiments, there is provided a composition comprising at least one TLR2-activating lipoprotein, or fragment or derivative thereof of the invention, for example a lipopeptide comprising the amino acid sequence of SEQ ID NO:13 or SEQ ID NO:14 which provides protective immunity to a subject.

In certain embodiments, the composition can comprise the at least one TLR2-activating lipoprotein, or fragment or derivative thereof, for example a lipopeptide comprising the amino acid sequence of SEQ ID NO:13 or SEQ ID NO:14 as the adjuvant and an antigen from the bacteria *B pertussis*.

In certain embodiments, the composition can comprise a tumour antigen for example a tumour specific or tumour-associated antigen.

In certain embodiments, the composition can be an acellular pertussis vaccine.

In certain further aspects the present invention provides a composition according to the invention for use in medicine.

In certain further aspects the present invention provides the use of at least one TLR2-activating lipoprotein, or fragment or derivative thereof of the invention, for example a lipopeptide comprising the amino acid sequence of SEQ ID NO:13 or SEQ ID NO:14 in the preparation of a medicament for the prevention or treatment of a condition caused by a pathogen, cancer or an allergic disease.

In certain further aspects, the present invention provides at least one TLR2-activating lipoprotein, or fragment or derivative thereof of the invention, for example comprising a lipopeptide comprising the amino acid sequence of SEQ ID NO:13 or SEQ ID NO:14 for use in the treatment or prevention of a condition caused by a pathogen, cancer or an allergic disease.

In certain embodiments, a pathogen can be any infectious agent, in particular a bacterium, a virus, a fungus or a parasite.

In certain embodiments, the pathogen can be *B. pertussis*.

In embodiments, tumourigenesis may be hepatic cancer, lung cancer, in particular non-small cell lung cancer, prostate cancer, ovarian cancer, breast cancer, melanoma, basal cell carcinoma, or haematological malignancies.

In certain embodiments, the allergic disease is asthma.

In certain embodiments, the at least one TLR2-activating lipoprotein, or fragment or derivative thereof of the invention, for example a lipopeptide comprising the amino acid sequence of SEQ ID NO:13 or SEQ ID NO:14 or the compositions containing the same are administered prophylactically to a subject. In certain further embodiments, the at least one TLR2-activating lipoprotein, or fragment or derivative thereof, for example a lipopeptide comprising the amino acid sequence of SEQ ID NO:13 or SEQ ID NO:14 or the compositions comprising the same are administered therapeutically. Prophylactic and therapeutic compositions may be administered to subjects in need thereof as required.

In various further aspects, the present invention extends to the at least one TLR2-activating lipoprotein, or fragment or derivative thereof of the invention, for example comprising a lipopeptide comprising the amino acid sequence of SEQ ID NO:13 or SEQ ID NO:14 or to preparations or mixtures comprising the same, or to compositions containing the same, for use as a booster to enhance the immune response generated in a host against a pathogen to which the subject has previously been exposed, typically by way of infection or due to the previous administration of a primary vaccine.

The invention further provides for the use of the at least one TLR2-activating lipoprotein, or fragment or derivative thereof, for example a lipopeptide comprising the amino acid sequence of SEQ ID NO:13 or SEQ ID NO:14 of the invention in a method of vaccinating a subject to induce immunity against infectious disease and in particular against *B. pertussis* derived infectious disease.

Accordingly a further aspect of the invention provides for a method of mediating an immune response in a subject against an infectious disease, said method comprising the steps of:
 providing a composition comprising at least one TLR2-activating lipoprotein, or fragment or derivative thereof of the invention, for example comprising a lipopeptide comprising the amino acid sequence of SEQ ID NO:13 or SEQ ID NO:14, and
 administering the composition to the subject in a therapeutically effective or prophylactically effective amount sufficient to elicit an immune response in the subject against the infectious disease.

According to a further aspect of the invention, there is provided a lipoprotein, or fragment or derivative thereof, of a first aspect of the invention for use in the preparation of a medicament for the treatment of a condition requiring enhancement of a Th1 and/or Th17 response in particular a pathogen or a malignant condition/cancer.

In certain embodiments of the aspects of the present invention, the composition can include an antigen from pathogen that causes an infectious disease. In certain embodiments the composition can include an antigen from a pathogen that causes tetanus, diphtheria, hepatitis B virus, polio, haemophilus influenza B, influenza, meningococcal disease Myobacterium tuberculosis. In certain embodiments the composition can include an antigen from a pathogen that causes a respiratory tract infection. In certain embodiments, the respiratory tract infection is from *B. pertussis* and causes whooping cough.

Accordingly a further aspect of the invention provides for a method of mediating an immune response in a subject with cancer, said method comprising the steps of:
 providing a composition comprising at least one TLR2-activating lipoprotein, or fragment or derivative thereof, for example comprising a lipopeptide comprising the amino acid sequence of SEQ ID NO:13 or SEQ ID NO:14, and
 administering the composition to the subject in a therapeutically effective or prophylactically effective amount.

In certain embodiments, the antigen can be a tumour-specific protein or peptide or killed whole tumor cells or extracts. In certain embodiments, the antigen can be a tumour associated antigen, a tumour specific antigen, a heat shock protein and antigenic peptide or a synthetic peptide antigen derived from or corresponding to that in a cancerous cell.

In embodiments of the aspects of the invention, the cancer can be melanoma or non-Small cell Lung Carcinoma, prostate cancer, ovarian cancer, breast cancer. melanoma, basal cell carcinoma, or haematological malignancies.

Accordingly a further aspect of the invention provides for a method of mediating an immune response in a subject with an allergic disease, said method comprising the steps of:
 providing a composition comprising at least one TLR2-activating lipoprotein, or fragment or derivative thereof, for example comprising a lipopeptide comprising the amino acid sequence of SEQ ID NO:13 or SEQ ID NO:14, and administering the composition to the subject in a therapeutically effective or prophylactically effective amount.

In certain embodiments, the allergic disease is asthma.

In embodiments of the aspects of the present invention, the composition can be a vaccine composition.

According to a further aspect, there is provided a lipoprotein, or fragment or derivative thereof, of the first aspect of the invention for use in mediating an immune system in a subject in particular for use in the treatment or conditions requiring enhancement of Th1 and/or Th17 responses, in particular a pathogen or a malignant condition/cancer.

As used herein, the term "vaccine composition" means any composition containing an immunogenic determinant which stimulates the immune system in a manner such that it can better respond to subsequent challenges or pathogenic infections or a tumour. It will be appreciated that a vaccine usually contains an immunogenic determinant and optionally an adjuvant, the adjuvant serving to non-specifically enhance the immune response to the immunogenic determinant.

In embodiments, the composition can be provided in combination with an immune modulator. In embodiments the immune modulator can be a Phosphoinositide kinase-3 (PI3K) inhibitor, a mitogen activated (MAP) kinase inhibitor or immune checkpoint inhibitors. In embodiments, the immune checkpoint inhibitors can be anti-Cytotoxic T-Lymphocyte Antigen 4 (CTLA4) or anti-Programme Death 1 (PD1)/Programmed Death Ligand-1 (PDL1).

Phosphoinositide kinase-3 (PI3K) is a proto-oncogene which regulates cell longevity. In one embodiment the pI3K inhibitor is LY294002, a pharmaceutically acceptable salt or solvate thereof, or an analogue thereof, wherein the analogue has pI3K inhibitory activity. Alternatively the pI3K inhibitor may be wortmannin (WMN) or a pharmaceutically acceptable salt or solvate thereof, or an analogue thereof.

MAP kinases are proteins which are involved with cellular responses, inflammation and growth. P38 kinase (p38) is a member of the stress activated protein kinase (SAPK) group of MAP kinases. In certain embodiments, the inhibitor is a p38 kinase inhibitor. Preferably the p38 kinase inhibitor is SB203580 or a pharmaceutically acceptable salt or solvate thereof, or an analogue thereof, wherein the analogue has p38 inhibitory activity. Alternatively the inhibitor may be SB220025 or SB239063 or a pharmaceutically acceptable salt or solvate thereof, or an analogue thereof, wherein the analogue has p38 kinase inhibitory activity.

BRIEF DESCRIPTION OF THE FIGURES

Embodiments of the present invention will now be described by way of example only with reference to the figures described below.

FIG. 1A shows SEQ ID NOs:1-6 which are full length sequences of *B. pertussis* lipoproteins BP1569, BP2992, BP0205, BP3342, BP3819 and BP2508. FIG. 1B shows SEQ ID NOs:7-12 which are N-terminal signal peptide sequences from putative *B. pertussis* lipoproteins (positively charged residues and putative lipobox are highlighted in bold, invariant cysteine residue is underlined). FIG. 1C shows SEQ ID NO:13 and SEQ ID NO:14 which are the sequences of the lipopeptides from *B. pertussis*.

FIG. 3A shows luciferase activity of HEK-293T cells stably expressing human TLR2 which were transfected with an NF-κB luciferase reporter construct prior to stimulation with increasing doses of BP1569. Luciferase activity was quantified after 24 h. FIG. 3B shows IL-8 production of HEK-293T cells stably expressing human TLR2 which were transfected with an NF-κB luciferase reporter construct prior to stimulation with increasing doses of BP1569. IL-8 production was quantified after 24 h. FIG. 3C shows phosphorylation of p38 which was assessed following stimulation of spleen cells from C3H/HeJ mice with BP1569 with or without addition anti-TLR2 antibody of (T2.5 2.5 µg/ml) or an isotype control. FIG. 3D shows IL-6 concentrations in supernatants of human PBMC which were treated with BP1569 (100 ng/ml) in the presence and absence of anti-TLR1 or anti-TLR6 neutralising antibodies. After 24 h, the concentrations of IL-6 in supernatants were determined by ELISA.

FIG. 4A shows IL-12 and IL-6 concentrations when C3H/HeJ mice were injected intraperitoneal (i.p.) with BP1569 in PBS (70 µg) or PBS only. After 3 h serum IL-12 and IL-6 concentrations were quantified by ELISA. FIG. 4B shows concentration of antigen-specific IFN-γ quantified by ELISA when C3H/HeJ mice were injected in the footpad with PBS or 10 µg of BP1569. After seven days the draining lymph node was harvested and cells were stimulated with BP1569 (2 µg/ml). FIG. 4C shows concentration of antigen-specific IFN-γ quantified by ELISA when C3H/HeJ mice were injected in the footpad with PBS or 10 µg of BP1569. After seven days the draining lymph node was harvested and cells were stimulated with total heat killed *B. pertussis* 1-100×10⁶/ml).

FIG. 5A shows TNF-α, IL-12p40, IL-12p70, IL-6 and IL1α production from dendritic cells from C57BL/6 mice which were stimulated with increasing concentrations of lipopeptides LP1569. Anti-TLR2 (T2.5 2.5 µg/ml) was co-incubated with the highest dose of peptide. After 24 hr culture, cytokine production was quantified by ELISA. FIG. 5B shows TNF-α production from dendritic cells from C57BL/6 mice were stimulated with LP1569 or LP1569 with anti-TLR2 (αTLR2; T2.5: 2.5 µg/ml). After 24 hr, TNF-α production was quantified by ELISA. FIG. 5C shows TNFα production from human PBMC which were treated with increasing concentrations of LP1569 for 24 hr and TNFα and IL-6 production was quantified by ELISA. FIG. 5D shows serum cytokines from C57BL/6 mice which were injected i.p. with 50 or 100 µg of LP1569. After 3 hr serum IL-6 and IL-12p40 were quantified by ELISA.

FIG. 6A shows spleen cells from C57BL/6 mice stimulated with LP1569 (100 ng/ml) or medium with or without anti-IL-12p40 (αp40) or anti-IL-23p19 (αp19) blocking antibodies. After 72 h supernatants were tested for IFN-γ by ELISA. FIG. 6B shows spleen cells from C57BL/6 mice stimulated with LP1569 (100 ng/ml) or medium with or without IL-1β or IL-23. After 72 h supernatants were tested for IL-17 by ELISA. FIG. 6C shows intracellular cytokine staining for IFN-γ gated on CD4 T cells from spleen cell cultures stimulated with LP1569 (100 ng/ml), IL-1β or both.

FIG. 7A shows CF (Difco Laboratories, Detroit, MI), Merck Adjuvant 65 (Merck and Company, Inc., USA), AS-2, AS01, AS03, A504, AS15 (GSK, USA), MF59 (Novartis, Sienna, Italy), CpG oligonucleotides, bioadhesives and mucoadhesives, microparticles, liposomes, outer membrane vesicles, polyoxyethylene ether formulations, polyoxyethylene ester formulations, muramyl peptides or imidazoquinolone compounds.

Figure 2A:
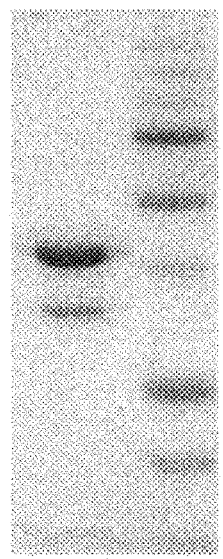
FIG. 2A shows an SDS-PAGE analysis of *Bordetella pertussis* lipoprotein BP1569 (lane 1: 10 ng BP1569, Lane 2: molecular weight markers) following nickel affinity and ion-exchange chromatography.

The TLR2-activating lipoprotein of the present invention may be administered to a patient in need of treatment via any suitable route. Typically, a composition of the invention can be administered parenterally by injection or infusion. Examples of preferred routes for parenteral administration include, but are not limited to; intravenous, intracardial, intraarterial, intraperitoneal, intramuscular, intracavity, subcutaneous, transmucosal, inhalation or transdermal. Routes of administration may further include topical and enteral, for example, mucosal (including pulmonary), oral, nasal, rectal.

In embodiments where the composition is delivered as an injectable composition, for example in intravenous, intradermal or subcutaneous application, the active ingredient can be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection or, Lactated Ringer's injection. Preservatives, stabilisers, buffers, antioxidants and/or other additives may be included, as required.

The composition may also be administered via microspheres, liposomes, other microparticulate delivery systems or sustained release formulations placed in certain tissues including blood.

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition ISBN 0-912734-04-3 and Pharmaceutical Dosage Forms and Drug Delivery Systems; Ansel, H. C. et al. 7th Edition ISBN 0-683305-72-7, the entire disclosures of which is herein incorporated by reference.

The composition of the invention is typically administered to a subject in a "therapeutically effective amount", this being an amount sufficient to show benefit to the subject to whom the composition is administered. The actual dose administered, and rate and time-course of administration, will depend on, and can be determined with due reference to, the nature and severity of the condition which is being treated, as well as factors such as the age, sex and weight of the subject being treated, as well as the route of administration. Further due consideration should be given to the properties of the composition, for example, its binding activity and in-vivo plasma life, the concentration of the antibody or binding member in the formulation, as well as the route, site and rate of delivery.

Dosage regimens can include a single administration of the composition, or multiple administrative doses of the composition. The compositions can further be administered sequentially or separately with other therapeutics and medicaments which are used for the treatment of the condition for which the TLR2-activating lipoprotein of the present invention is being administered to treat.

Examples of dosage regimens which can be administered to a subject can be selected from the group comprising, but not limited to; 1 µg/kg/day through to 20 mg/kg/day, 1 µg/kg/day through to 10 mg/kg/day, 10 µg/kg/day through to 1 mg/kg/day. In certain embodiments, the dosage will be such that a plasma concentration of from 1 µg/ml to 100 m/ml of the lipoprotein is obtained. However, the actual dose of the composition administered, and rate and time-course of administration, will depend on the nature and severity of the condition being treated. Prescription of treatment, e.g. decisions on dosage etc, is ultimately within the responsibility and at the discretion of general practitioners and other medical doctors, and typically takes account of the disorder to be treated, the condition of the individual patient, the site of delivery, the method of administration and other factors known to practitioners.

Definitions

Unless otherwise defined, all technical and scientific terms used herein have the meaning commonly understood by a person who is skilled in the art in the field of the present invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

As used herein, terms such as "a", "an" and "the" include singular and plural referents unless the context clearly demands otherwise. Thus, for example, reference to "an active agent" or "a pharmacologically active agent" includes a single active agent as well as two or more different active agents in combination, while references to "a carrier" includes mixtures of two or more carriers as well as a single carrier, and the like.

As used herein, the term "treatment" and associated terms such as "treat" and "treating" means the reduction of the progression, severity and/or duration of Whooping Cough or at least one symptom thereof, wherein said reduction or amelioration results from the administration of a TLR2-activating lipoprotein of B. pertussis. The term 'treatment' therefore refers to any regimen that can benefit a subject. The treatment may be in respect of an existing condition or may be prophylactic (preventative treatment). Treatment may include curative, alleviative or prophylactic effects. References herein to "therapeutic" and "prophylactic" treatments are to be considered in their broadest context. The term "therapeutic" does not necessarily imply that a subject is treated until total recovery. Similarly, "prophylactic" does not necessarily mean that the subject will not eventually contract a disease condition.

As used herein, the term "subject" refers to an animal, preferably a mammal and in particular a human. In a particular embodiment, the subject is a mammal, in particular a human. The term "subject" is interchangeable with the term "patient" as used herein.

As used herein, the terms "mount", "mounted", "elicit" or "elicited" when used in relation to an immune response mean an immune response which is raised against the immunogenic determinant of a vaccine composition which is administered to a subject. Typically the immunogenic determinant of the vaccine composition comprises the at least one lipoprotein of the present invention.

As used herein, the term "immune response" includes T cell mediated and/or B cell mediated immune responses that are influenced by modulation of T cell co-stimulation. The term immune response further includes immune responses that are indirectly effected by T cell activation such as antibody production (humoral responses) and the activation of cytokine responsive cells such as macrophages.

The inventors of the present invention have identified novel TLR2 lipoprotein ligands from *B. pertussis* capable of activating innate immune responses that drive the induction of protective adaptive cellular immunity. Additionally, the present inventors have demonstrated that these novel proteins specifically activate TLR2 and drive potent pro-inflammatory cytokine production.

A number of Gram negative bacteria have been shown to express ligands for TLR2. TLR2 forms a heterodimer with either TLR1 or TLR6 to recognize triacylated or diacylated lipoproteins, respectively. These lipoproteins contain a common N-terminal signal sequence comprising a positively charged region followed by a hydrophobic region of 7-22 residues and finally a lipobox within the first 40 residues from the N-terminus with the consensus sequence [LVI][ASTVI][ASG][C]. Without being bound by theory, the inventors submit that during biosynthesis of the lipoprotein of the present invention, an acyl group such as palmytic acid or a diacylated lipid is covalently attached to the conserved cysteine residue in the lipobox and the signal sequence is enzymatically cleaved, leaving an exposed acyl coupled N-terminus. The acyl group on a lipopeptide physically interacts with TLR2 to activate the receptor and subsequent downstream signalling pathways. Preferably the lipoproteins of the present invention can be triacylated because activity can be blocked with neutralising antibodies to TLR1 and TLR2 but not TLR6. This is because TLR1/2 heterodimers recognize triacylated lipoproteins whereas TLR2/6 heterodimers recognize diacylated lipoproteins.

The proteins identified in the present invention contain unique N-terminal signal peptide characteristic of bacterial lipoproteins from Gram negative bacteria. It is demonstrated that BP1569 and BP2992 have potent immunostimulatory activity, driving DC maturation and pro-inflammatory cytokine production. Furthermore, the present inventors have demonstrated that the corresponding synthetic lipopeptide agonist of TLR2, LP1569, is an effective adjuvant for an experimental acellular pertussis vaccine (Pa) that induced Th1 and Th17 responses and conferred a high level of protection against *B. pertussis* infection of the respiratory tract in mice.

Host immunity to *B. pertussis* involves a combination of innate and adaptive immune responses. The induction of Th1 and Th17 cells is dependent on dendritic cell maturation and production of innate cytokines, including IL-12, and IL-1, IL-6 and IL-23 respectively. The induction of DC maturation and cytokine production is driven by activation through PRR, including TLRs and NLRs. Indeed it has been demonstrated that TLR4 plays a critical role in natural and vaccine-induced protective cellular immunity to *B. pertussis*. Surprisingly, during *B. pertussis* infection Th1 responses were stronger in TLR4-defective mice when compared with wildtype mice and this was attributed to weaker Treg cells responses due to the loss of TLR-4-induced innate IL-10 (Higgins S C, et al.). It has been suggested that *B. pertussis* must contain other IL-12-inducing PAMPs that promote Th1 responses. The present study demonstrates that TLR2 ligands including BP1569 induce potent IL-12 production by DC and macrophages and promote Th1 responses to an experimental Pa and may therefore impart drivers of protective Th1 responses in natural host immunity to *B. pertussis*.

In addition to the well established function of Th1 cells in protective immunity to *B. pertussis*, by virtue of their in role in macrophage activation and opsonising antibody production, evidence is emerging that Th17 cells also play a role in immunity to *B. pertussis* through recruitment and activation of neutrophils in the respiratory tract (Ross P J, et al.). The present inventors have demonstrated that Adenylate Cyclase Toxin (ACT) from *B. pertussis* promotes Th17 responses by inducing IL-1β production via activation of the NLRP3 inflammasome and caspase-1 which is required for cleavage of pro-IL-1β (Dunne A, et al.). The induction of pro-IL-1β is driven through a TLR-induced NFκB pathway. IL-1β synergises with IL-23 to induce expansion of Th17 cells but also promotes innate IL-17 production by γδ T cells. TLR agonists have also been shown to induce IL-17 production by γδ T cells. IL-17-secreting γδ T cells play an important role early in infection and help to drive IL-17 production by CD4 T cells. The present inventors have demonstrated that the TLR2 liptoide LP1569 induces IL-12 which promotes IFN-γ production by CD4 and CD8 T cells. LP1569 induced significant IL-17 in combination with IL-23. IL-1 and IL-23 are required to induce IL-17 production by γδ T cells, and the lack of IL-17 production in vitro without exogenous IL-23 may reflect the fact that LP1569 is more effective at inducing IL-1 than IL-23. Furthermore, it promoted IL-17 production by CD4 T cells in vivo when used as an adjuvant for an experimental Pa.

Immunity to infection by *B. pertussis* conferred by vaccination with Pa wanes significantly over a relatively short period; the efficacy of the vaccines has been shown to be as low as 24% in children aged 8 to 12 years (and this may explain the recent resurgence of whopping cough). Current Pa administered with alum as the adjuvant and studies in mice and humans have shown that these vaccines preferentially induce Th2-type responses. However, recent studies in mice and baboons have suggested that a failure of Pa to induce Th1 or Th17 responses may explain their limited ability to prevent infection with *B. pertussis* (Ross P J, et al.). The present inventors demonstrate that the use of a Th1/Th17 promoting adjuvant such the TLR2 agonists BP1569 or BP2992 or their corresponding synthetic lipopeptides LP1569 and LP2992 have the capacity to improve the efficacy of current Pa by promoting the induction of protective cellular immunity. Furthermore, since these lipoproteins are *B. pertussis* antigens as well as adjuvant TLR2 agonists they have considerable potential for inclusion in a more effective vaccine against *B. pertussis*.

The inventors of the present invention have used mass spectroscopy and bioinformatic approaches to identify six putative TLR-activating lipoproteins from *B. pertussis* (Table 1).

TABLE 1

Putative lipoproteins from *Bordetella pertussis*.

| Name | Primary Accession | Electronic Annotation | Size | Similar to |
| --- | --- | --- | --- | --- |
| BP0205 | Q7W0D8 | Putative lipoprotein | ~19 kDa | Hypothetical protein Q56428 From *Thermus thermophilis* |
| BP1569 | Q7VXZ9 | Putative lipoprotein | ~40 kDa | Lipoprotein NMB0928 from *Neisseria menigitidis* |

TABLE 1-continued

Putative lipoproteins from *Bordetella pertussis*.

| Name | Primary Accession | Electronic Annotation | Size | Similar to |
|---|---|---|---|---|
| BP3342 | Q7VU04 | Putative lipoprotein | ~16 kDa | Lipoprotein Omp P6 from *Haemophilus influenzae* (Verified TLR2 agonist (14); 39% sequence identity) |
| BP3819 | Q7VSV3 | Uncharacterized | ~25 kDa | Poor matches |
| BP2508 | Q9X6Z0 | Putative lipoprotein Synonym: OmlA | ~19 kDa | Lipoprotein OmlA from *Burkholderia pseudomallei* |
| BP2992 | Q7VUT2 | Putative lipoprotein | ~16 kDa | Outer membrane lipoprotein PCP from *H. influenzae* (Verified TLR2 agonist (14); 40% sequence identity) |

The inventors demonstrate that at least two of these novel proteins specifically activate TLR2 and drive potent pro-inflammatory cytokine production (BP1569 and BP2992). These proteins contain a characteristic N-terminal signal peptide that is unique to Gram negative bacteria. Table 2 shows SEQ ID NOs:7-12 which are the N-terminal signal peptides of these putative lipoproteins from *B. pertussis*.

```
(LP1569)
                                       SEQ ID NO: 7
MRMNK R HAGASALMALAL LAGC (LP2992)
                                       SEQ ID NO: 8
MNYMHSPSVVAGRARRLLAVAAVAGSVAV LAGC (LP0205)
                                       SEQ ID NO: 9
MQLTIR K LAYTLAFSTLV LAGC (LP3342)
                                       SEQ ID NO: 10
MKSRIA K SLTIAALAAT LAAC (LP3819)
                                       SEQ ID NO: 11
MSAPLDTPALRLNTRFATGIVLAGTLA LAGC (LP2508)
                                       SEQ ID NO: 12
MIARISLRPL K GLAVAVLAASA LTAC
```

TABLE 2

N-terminal signal peptide of putative lipopetides from *B. pertussis*

| Name | N-terminal signal peptide |
|---|---|
| LP1569 | MRMNK R HAGASALMALAL LAGC (SEQ ID NO: 7) |
| LP2992 | MNYMHSPSVVAGRARRLLAVAAVAGSVAV LAGC (SEQ ID NO: 8) |
| LP0205 | MQLTIR K LAYTLAFSTLV LAGC (SEQ ID NO: 9) |
| LP3342 | MKSRIA K SLTIAALAAT LAAC (SEQ ID NO: 10) |
| LP3819 | MSAPLDTPALRLNTRFATGIVLAGTLA LAGC (SEQ ID NO: 11) |
| LP2508 | MIARISLRPL K GLAVAVLAASA LTAC (SEQ ID NO: 12) |

The present inventors have demonstrated that BP1569 and BP2992 activate murine dendritic cells and macrophages and human mononuclear cells via TLR2. Furthermore, the inventors have demonstrated that the corresponding synthetic lipopeptides LP1569 and LP2992 have potent immunostimulatory and adjuvant properties, capable of enhancing Th1, Th17 and IgG2a antibody responses induced in mice with an experimental acellular pertussis vaccine and conferred protective immunity against respiratory infection with *B. pertussis*.

Furthermore, the inventors consider that the lipoproteins of the present invention can be utilised with kinase inhibitors and/or tumour associated antigens to provide a Th1/Th17 mediated response against tumours.

The present inventors have demonstrated that therapeutic administration of the synthetic lipopeptide LP1569 slows tumour growth and enhances survival in a murine colon cancer model. The lipoproteins of the present invention have considerable potential as therapeutics alone or in combination with PI3K kinase inhibitors or other inhibitors of regulatory responses or for inclusion in prophylactic and/or therapeutic vaccines for the treatment and prevention of cancer.

The present inventors predict that the lipopeptides of the present invention can be used as a therapeutic or as a vaccine composition in the treatment and/or prevention of allergic diseases such as asthma. This may relate to IFN-gamma mediated suppression of the Th2/Th17 response or IL-10-mediated suppression. In experiments carried out by the inventors, IFN-gamma induction and some IL-10 production are detected by the TLR2-activated dendritic cells. There are also reports that TLR2 agonists can induce/activate Treg cells.

The present invention will now be described with reference to the following examples which are provided for the purpose of illustration and are not intended to be construed as being limiting on the present invention.

EXAMPLES

MATERIALS AND METHODS

Mice

C57BL/6 mice and C3H/HeJ mice containing a mutation in the tlr4 gene were obtained from Harlan UK and maintained at Trinity College Dublin in a specific pathogen-free facility.

Reagents

Lipases from Aspergillus and *Pseudomonas* were obtained from Sigma. ELISA for TNF, IL-23, IL-10 and IL-17 were obtained from R&D. ELISA for IFN-γ, IL-6 and IL-12p40 were obtained from BD Biosciences. Lipopeptide LP1569 were synthesized by EMC Microcollections.

Cloning and Purification of BP1569 and BP2992

DNA encoding BP1569 and BP2992 was amplified from *B. pertussis* genomic DNA and cloned into the pET21a bacterial expression vector (Invitrogen) following sequence verification. C-terminal histidine versions were generated in *E. coli* BL21 pLysS cells following 0.2 mM IPTG induction for 18hr at 30° C. Cells were lysed using Bugbuster (Novagen) and proteins were subsequently purified by nickel affinity followed by DEAE ion-exchange chromatography. Following desalting on PD10 columns (GE healthcare), protein purity was determined by SDS-PAGE and coomassie staining or western blotting for the histidine tagged proteins.

Cell Preparation and Stimulation

Bone marrow derived dendritic cells (DCs) were prepared by culturing bone marrow cells obtained from the femur and tibia of mice in complete RPMI (cRPMI, RPMI containing 10% fetal calf serum, 100 U/ml penicillin, 100 μg/ml streptomycin, 2 mM 1-glutamine (Invitrogen), and 50 μM 2-ME (Sigma-Aldrich) supplemented with GM-CSF 40 ng/ml. Cells were re-cultured with fresh medium containing 40 ng/ml GM-CSF every 3 d for a period of 8 d. DC were seeded at $1\times10^6$ cells per ml 24 hr prior to stimulation. ELISA assays were performed using R&D kits according to the manufacturer's instructions. Spleen cells from C3H/HeJ mice were seeded at $2\times10^6$ cells per ml and stimulated with $Pam_3Cys_4$ (120nM) or BP1569 (120 nM) for the indicated times, with or without addition of T2.5-anti-TLR2 antibody or an isotype control (Hycult Biotech). For p38 activation assays, samples were lysed with RIPA buffer and SDS-PAGE was performed followed by Western blotting with anti-phospho-p38 and β-actin antibodies (Cell Signaling).

Luciferase Assay

HEK 293T cells stably expressing human TLR2 were transfected with an NF-κB luciferase construct as described previously (21) and stimulated overnight with the indicated concentrations of BP1569.

Flow Cytometry

Following stimulation, DC were stained with CD11c (clone N418; eBioscience), MHCII (clone M5/114.15.2 ebioscience), CD80 (clone 16-10A1 eBioscience) and CD86 (clone 16-10A1 eBioscience). Samples were analyzed with a FACS DIVA and FloJo software.

Cytokine Induction In Vivo

Figures 4A, 4B, 4C:
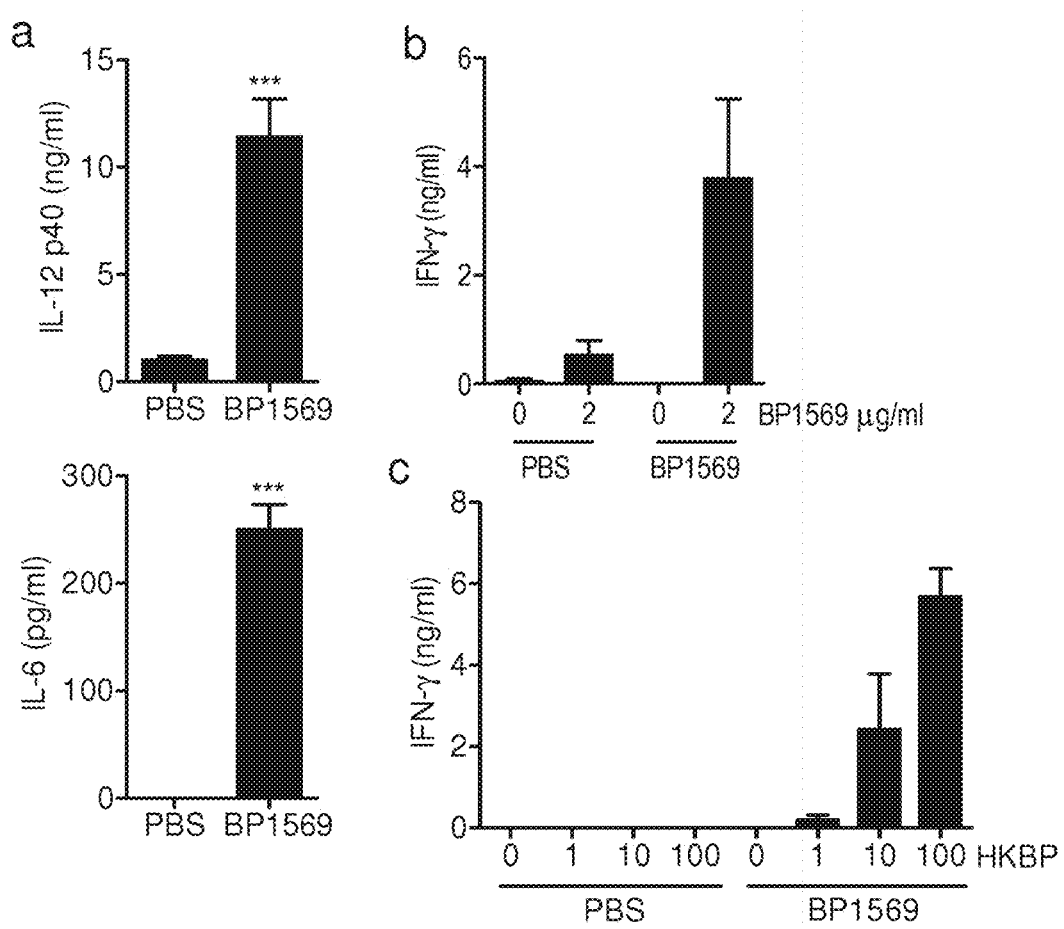
FIGS. 4A-4C demonstrate how BP1569 induces innate cytokine and antigen-specific IL-17 and IFN-γ production in vivo.
Figure 5A:
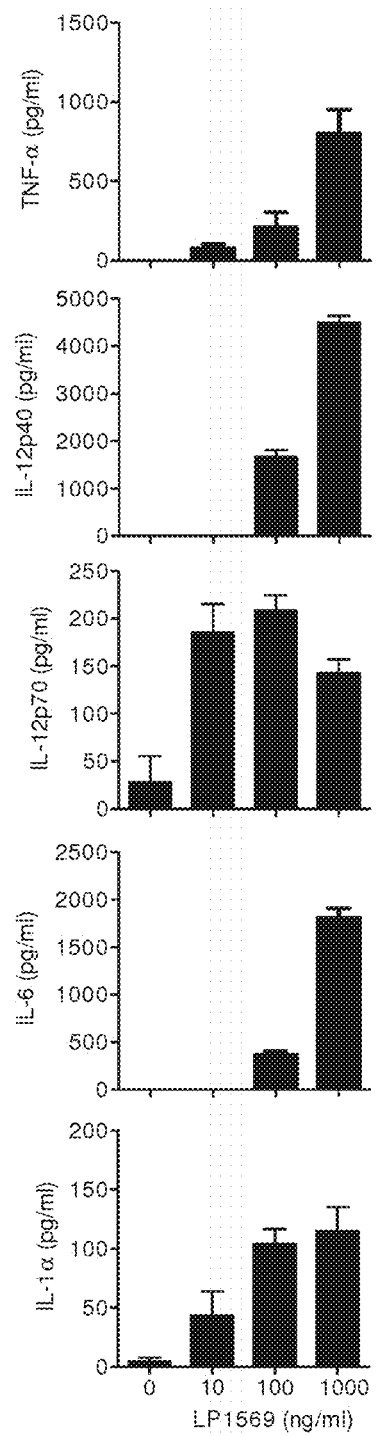
FIGS. 5A-5D demonstrate how synthetic lipopeptide LP1569 induces cytokine production by mouse Dendritic Cells and macrophage and human PBMC.
Figure 5B:
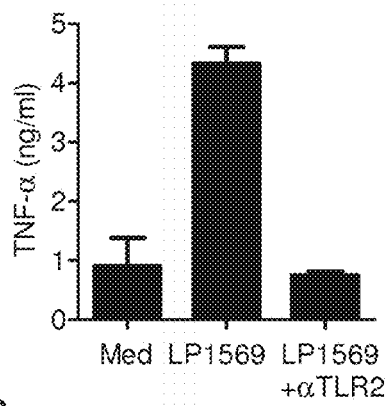
Figure 5C:
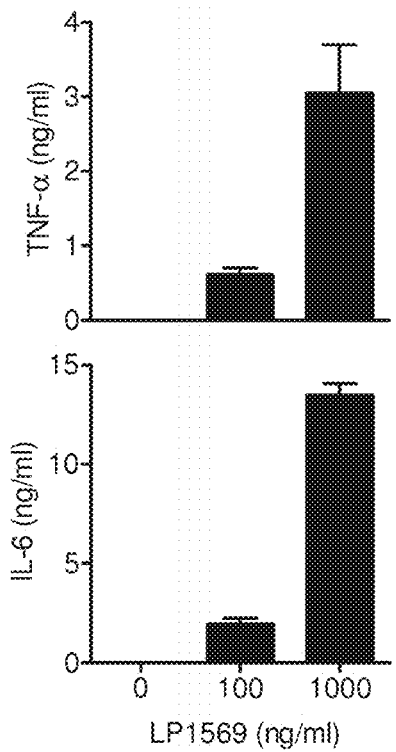
Figure 5D:
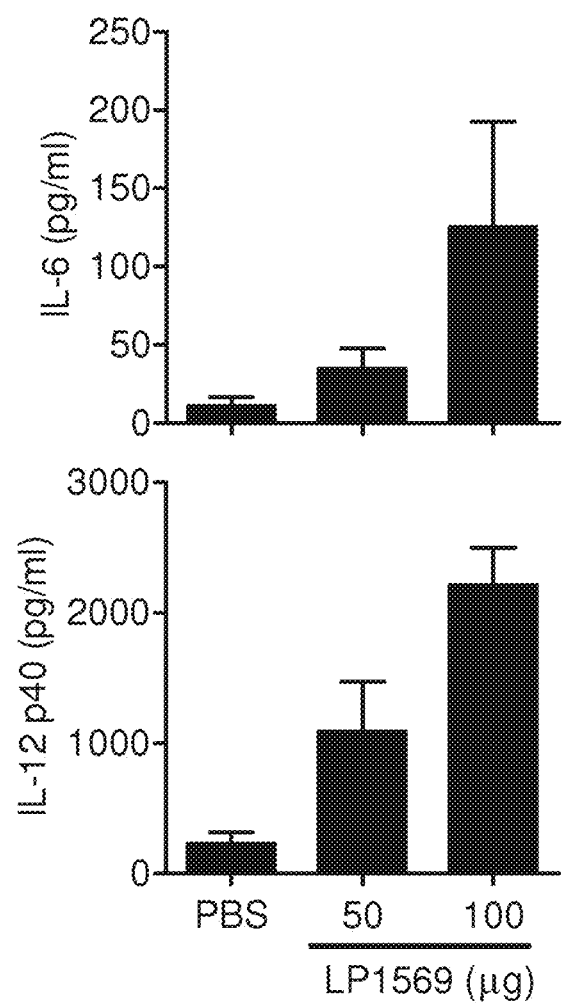
Figure 6A:
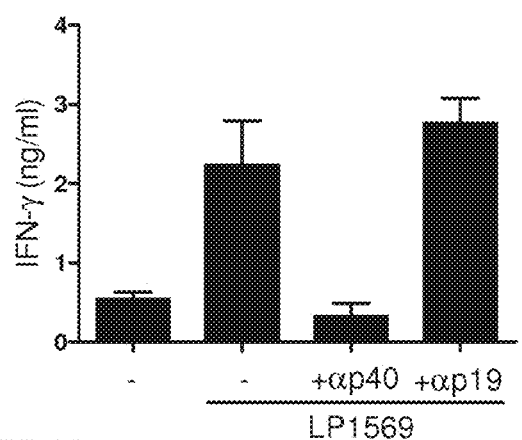
FIGS. 6A-6C demonstrate how LP1569 enhances activation of γδ T cells and CD4 T cells.
Figure 6B:
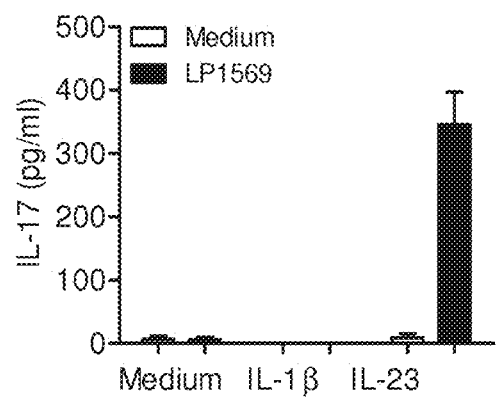
Figure 6C:
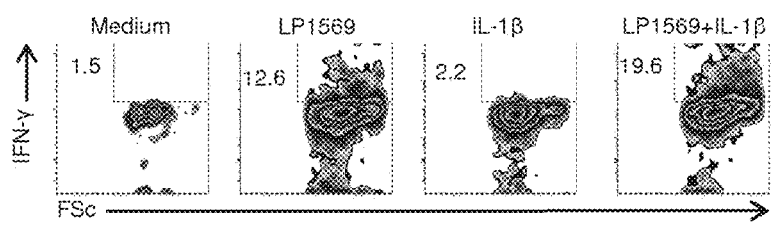
Figure 6D:
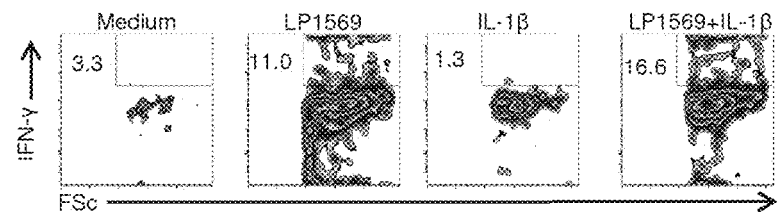
FIG. 6D shows intracellular cytokine staining for IFN-γ gated on CD8 T cells from spleen cell cultures stimulated with LP1569 (100 ng/ml), IL-1β or both.
Figure 6E:
FIG. 6E shows intracellular cytokine staining for IL-17 gated on γδ T cells from spleen cell cultures stimulated with LP1569, IL-23 or both.
Figure 7A:
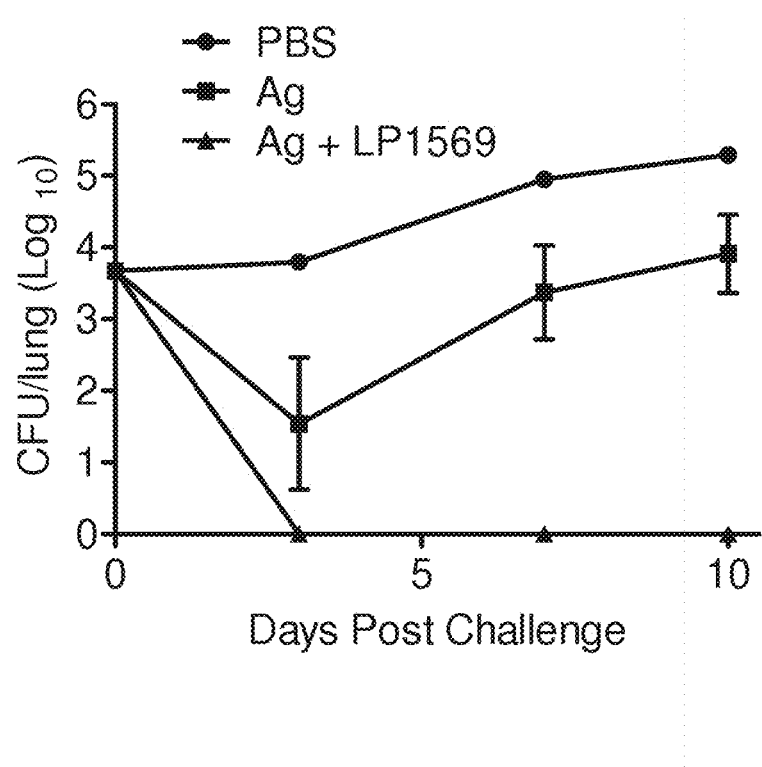
FIGS. 7A-7C demonstrate how LP1569 acts as an adjuvant for an experimental acellular *pertussis* vaccine and promotes protective cellular immunity against *B. pertussis*. C57BL/6 mice were immunized twice (0 and 4 weeks) with PTd, FHA and pertactin alone or formulated with LP1569 or PBS as control. Two weeks after the second immunization, mice were challenged by aerosol exposure to *B. pertussis*.
Figures 7B, 7C:
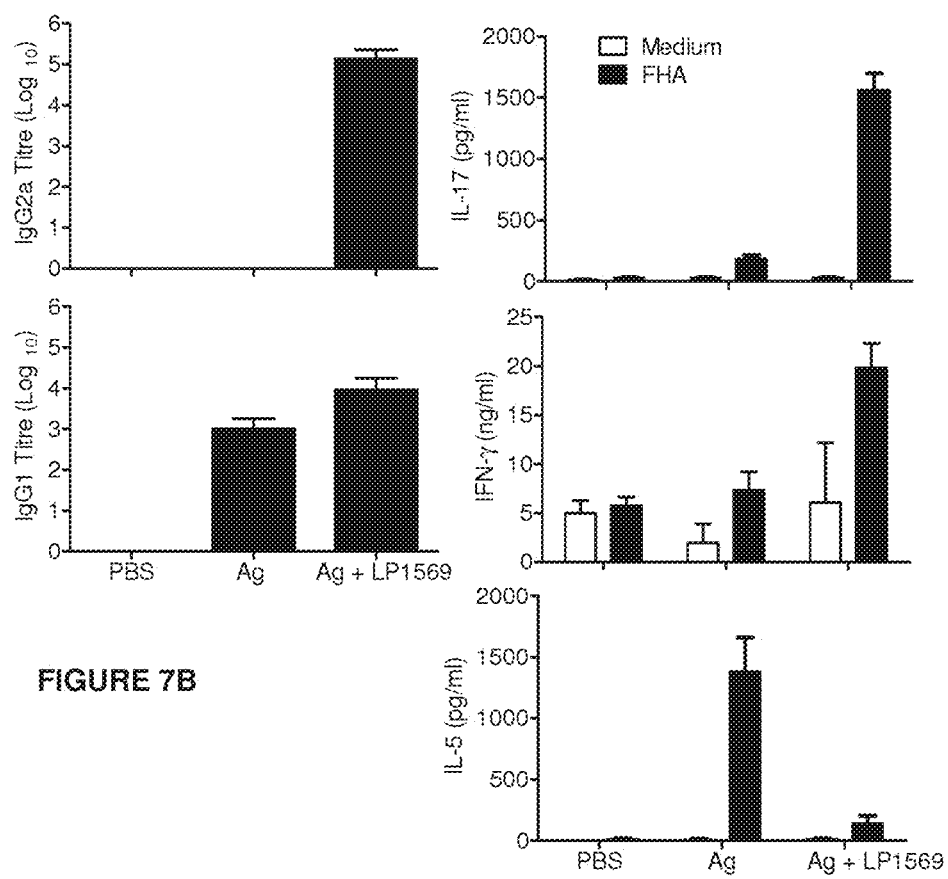
Figure 10A:
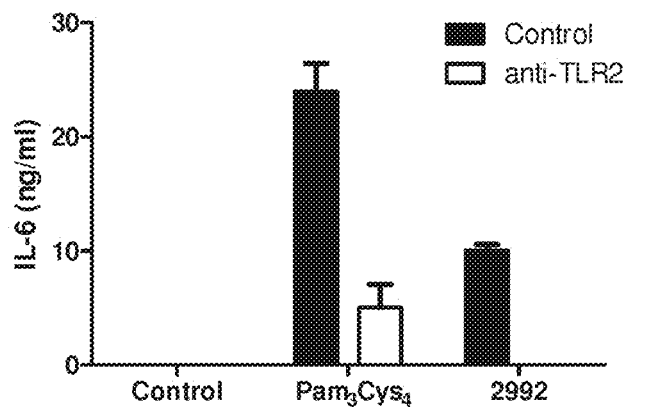
Figure 10B:
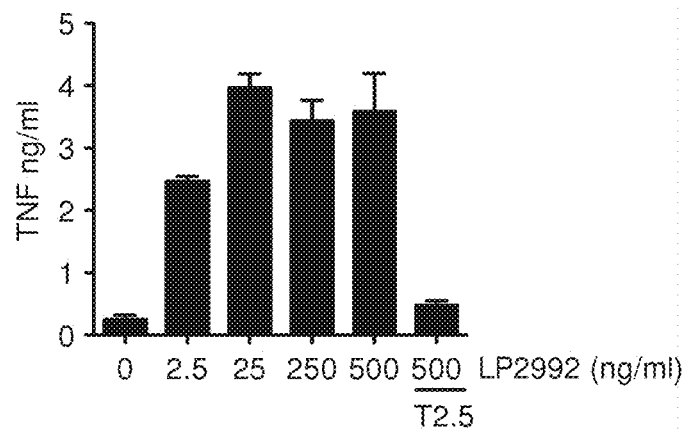
Figure 11:
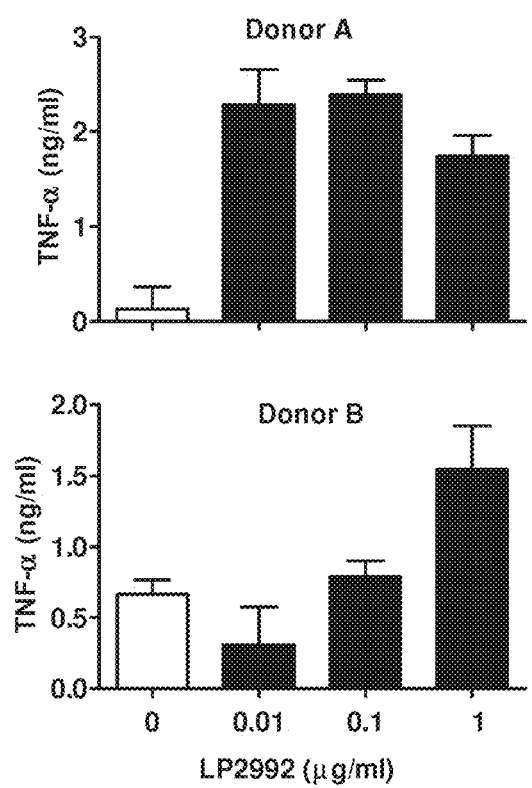
Figure 12C:
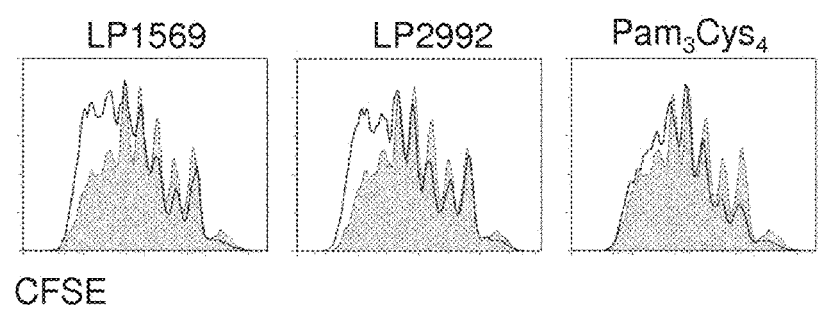
Figure 13:
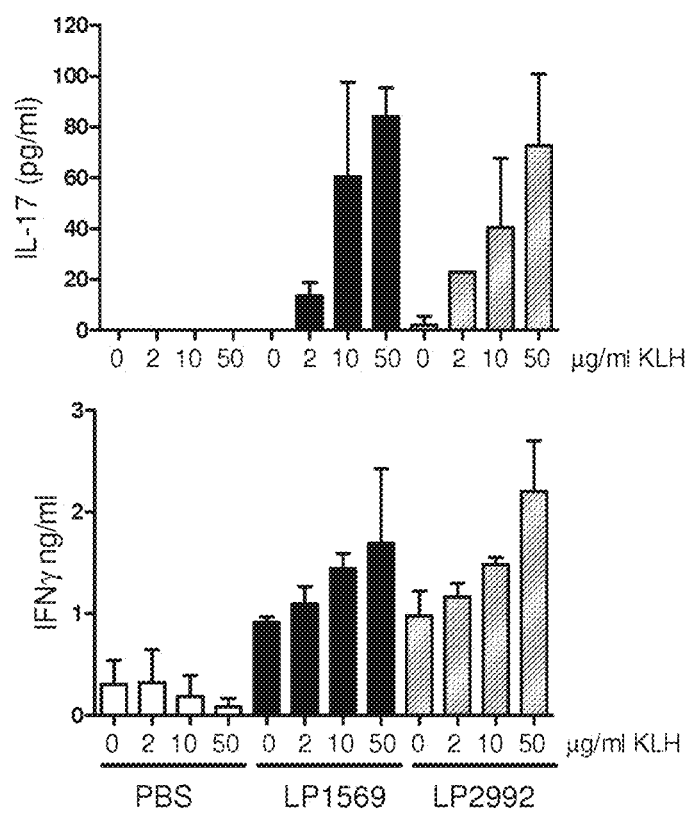
Figure 14A:
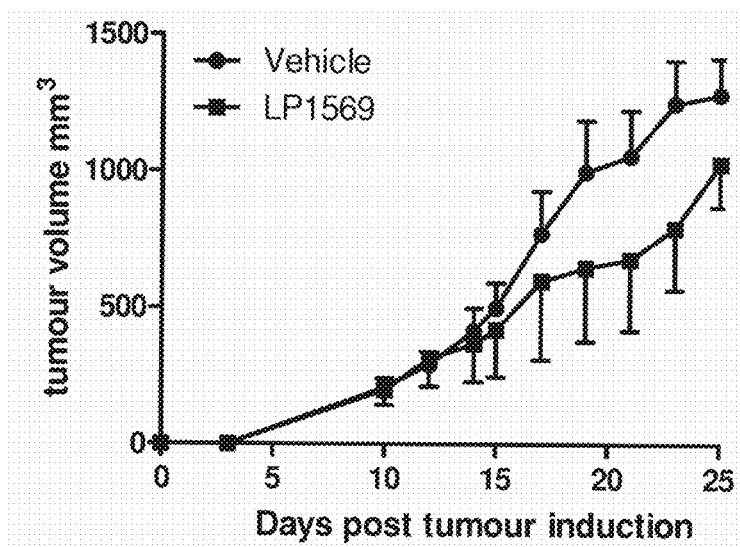
Figure 14B:
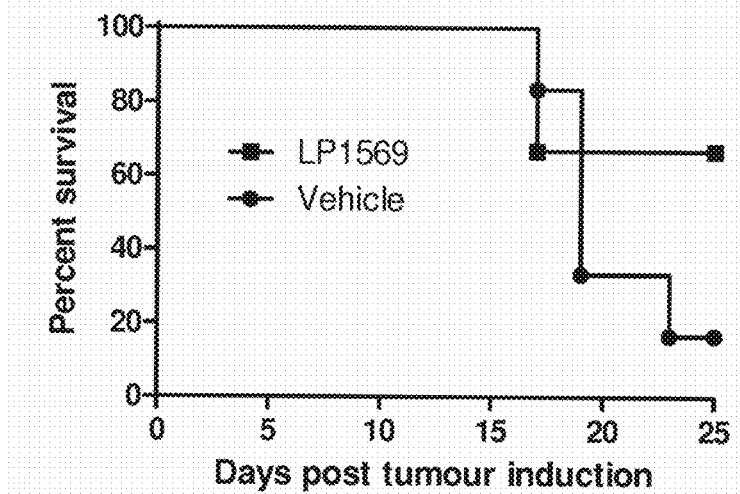

C3H/HeJ mice were treated intraperitoneally with BP1569 (70 μg) or PBS control and serum cytokines were measured by ELISA after 3h. Significant concentrations of IL-6 and IL-12 were detected in the serum of mice treated with the BP1569 versus PBS controls (FIG. 4A).

Antigenicity of BP1569

C3H/HeJ mice were injected into the footpad with BP1569 (10 μg) diluted in PBS or with PBS only. After seven days the draining lymph node was harvested and the lymph node cells were stimulated with either BP1569 (2 μg/ml) or heat killed *B. pertussis* pertussis ($1\text{-}100\times10^6$/ml). After 3 days of culture, the concentration of IFN-γ in supernatants was quantified by ELISA. BP1569-specific IFN-γ was induced at significant levels in mice immunized with BP1569 but not in mice immunized with PBS (FIG. 4B). Furthermore, cells from immunized mice produced IFN-γ upon re-stimulation with heat killed *B. pertussis*, thus providing evidence that BP1569 is an antigenic component of the bacteria (FIG. 4C).

Adjuvant Activity of BP1569

Mice were immunized i.p. twice (wk 0 and 4) with an experimental laboratory prepared Pa using two purified antigens, detoxified PT and FHA (1 and 2.5 μg/mouse respectively). PT was detoxified with formaldehyde as described (Sutherland et al). FHA was purchased from Kaketsuken, Kumamoto, Japan. Both preparation were highly purified, as determined by SDS gel chromatography and were free of detectable LPS. Mice were challenged with *B. pertussis* by aerosol inoculation or sacrificed 2 wks after second immunization.

*B. pertussis* Respiratory Challenge

Mice were infected with *B. pertussis* by exposure to an aerosol of live *B. pertussis* as previously described (22). The course of *B. pertussis* infection was followed by performing CFU counts on lungs from groups of 4 mice at intervals after challenge. The lungs were aseptically removed and homogenised in 1 ml of sterile physiological saline with 1% casein on ice. Undiluted and serially diluted homogenate (100 μl) from individual lungs was spotted in triplicate onto Bordet-Gengou agar plates, and the number of CFU was calculated after 5 days incubation at 37° C. The limit of detection was approximately $0.3 \log_{10}$ CFU per lung for groups of 4 mice at each time point

T Cell Cytokine Production

Spleen cells ($2\times10^6$/ml) from immunized mice were cultured at 37° C. and 5% $CO_2$ with heat killed *B. pertussis* or purified FHA. Stimulation with PMA (250 ng/ml; Sigma) and anti-mouse CD3 (1 μg/ml; Pharmingen, San Diego, USA) or medium only was used as positive and negative controls respectively. Supernatants were removed after 72 h and IL-4, IL-13, IL-17 and IFN-γ concentrations determined by two-site ELISA.

FHA-Specific Antibody Production

Serum antibody responses to *B. pertussis* were quantified by ELISA using plate-bound FHA (5 μg/ml). Bound antibodies were detected using biotin-conjugated anti-mouse IgG1 or IgG2a (Caltag) and peroxidase-conjugated streptavidin (BD Pharmingen). Antibody levels are expressed as the mean endpoint titre (±SE), determined by extrapolation of the linear part of the titration curve to 2 SE above the background value obtained with non-immune mouse serum.

Example 1

Identification, Cloning, Expression and Purification of TLR2-Activating Lipoproteins From *B. pertussis*

Putative *B. pertussis* lipoproteins were identified using the DOLOP database (http://www.mrc-lmb.cam.ac.uk/genomes/dolop) which searches for the presence of the N-terminal signal peptide found in lipoproteins from Gram-negative bacteria. The sequences of uncharacterised proteins identified in a mass spectroscopy analysis of secreted proteins from *B. pertussis* were used as a source for this screen in order to ensure that the proteins identified are indeed expressed proteins. The highest scoring proteins are listed in Table 1 alongside putative homologs from other bacterial species.

All six proteins contain the characteristic positively charged region followed by a stretch of hydrophobic amino acids and the lipobox containing the invariant cysteine residue to which the acyl group is attached during biosynthesis (FIG. 1). BR1569, BP2509 and BP2992 share some sequence similarity with lipoproteins from *Neisseria Meningitidis*, *Burkholderia pseudomallei* and *Haemophilis Influenzae* respectively.

C-terminal histidine versions of the putative lipoproteins were constructed and expressed in *E. coli* by IPTG induction. BP1569 and BP2992 were successfully expressed and purified by nickel affinity followed by ion-exchange chromatography. Although BP2992 was found to be an immunologically active ligand for TLR2 (data not shown), the present inventors decided to focus on BP1569 because its expression levels were higher and they could generate significant quantities of the lipoprotein for more extensive in vitro and in vivo studies. Analysis of the purity of the BP1569 preparation revealed a strong band at 40 kDa, with a weaker band at about 35 kDa (FIG. 2A). Western blotting suggested that the second band is a breakdown product of the full length protein as a result of proteolysis that was not prevented by the presence of protease inhibitors. The lipoproteins were co-purified with LPS, some of which we could remove using polymyxin B columns, but because of the sticky nature of the lipopeptides, it proved impossible to obtain a preparation completely free of LPS. Therefore, the inventors adopted a strategy of carrying out all initial studies with lipoproteins in TLR4 defective cells or mice and then synthesized lipopeptide versions of the lipoproteins for more thorough immunological analysis.

Example 2

BP1569 Induces DC Maturation and Cytokine Production in a TLR2 Dependent Manner

Figure 2B:
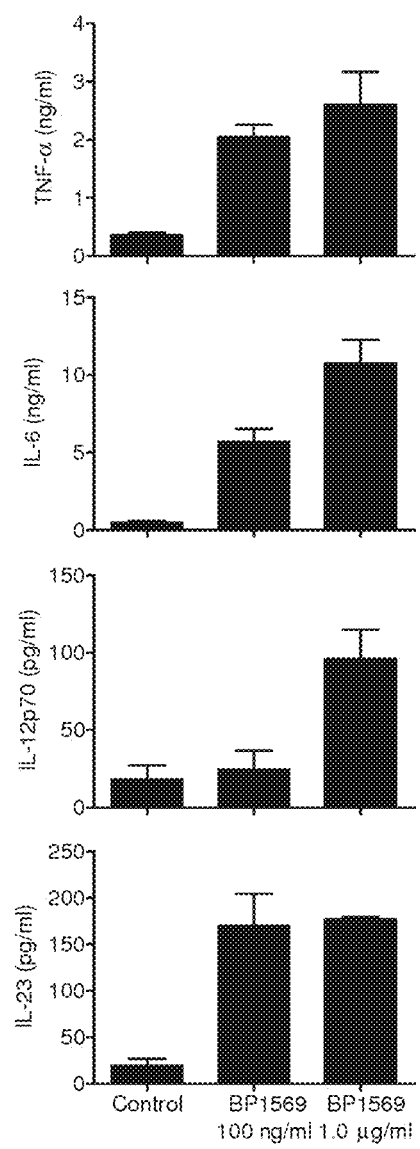
FIG. 2B shows cytokine production (TNF-alpha, IL-6, IL-12p70, IL-23) measured by ELISA when Dendritic Cells from C3H/HeJ mice were cultured with BP1569 (100 and 1000 ng/ml) for 24 h.
Figure 2C:
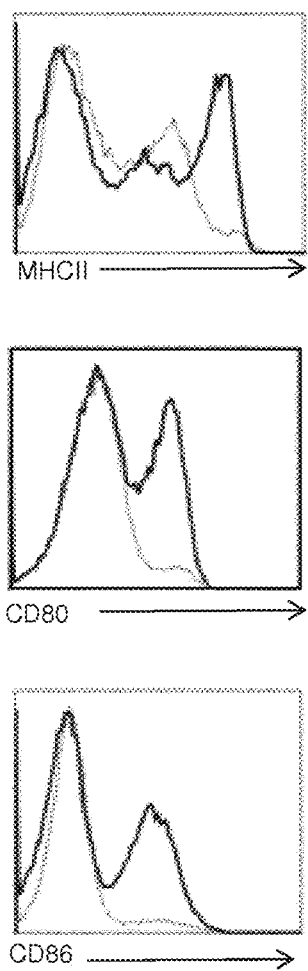
FIG. 2C shows surface expression of MHCII, CD80 and CD86 determined by flow cytometry following treatment of C3H/HeJ Dendritic Cells with BP1569 (100 ng/ml; bold line) or medium only (grey line) for 24h.

The present inventors examined the capacity of *pertussis* lipoprotein to activate innate immune cells in vitro using bone marrow-derived DCs from TLR4-defective C3H/HeJ mice. BP1569 induced robust IL-6, IL-12, IL-23 and TNF-α production by DC from C3H/HeJ mice (FIG. 2B). Furthermore, stimulation of DCs with BP1569 for 24 hours enhanced surface expression of MHC class II, CD80 and CD86 detectable by flow cytometry (FIG. 2C).

Figure 2D:
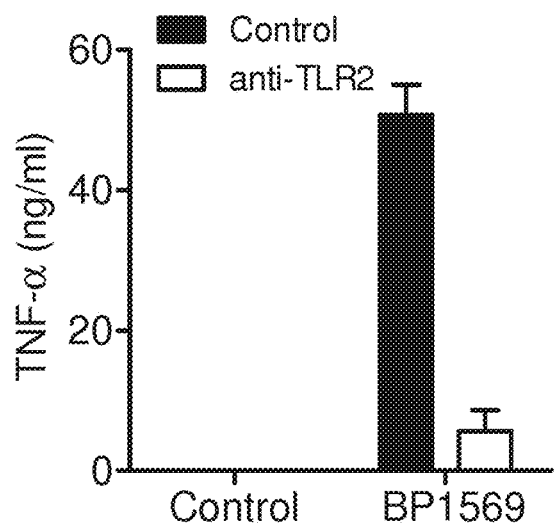
FIG. 2D shows TNF-α production measured by ELISA when Dendritic Cells from C3H/HeJ mice were treated with BP1569 (100 ng/ml) for 24 h with or without addition of anti-TLR2 antibody (T2.5; 2.5 µg/ml).
Figure 2E:
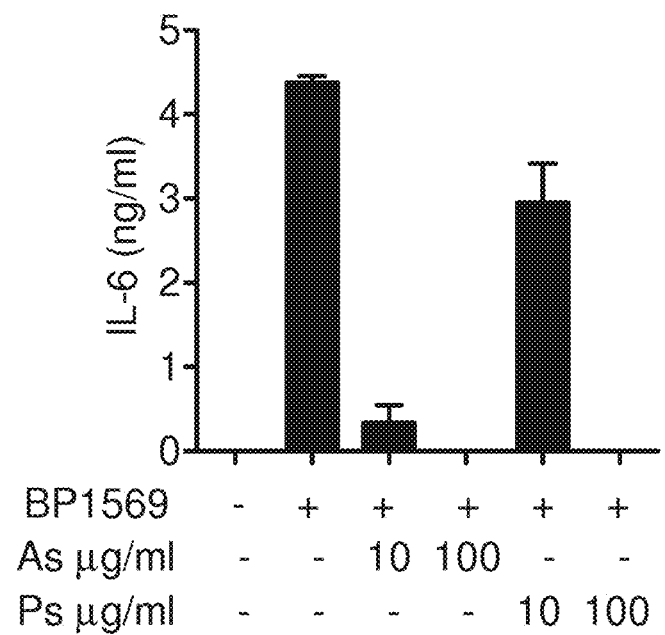
FIG. 2E shows concentrations of IL-6 in supernatants quantified by ELISA when BP1569 was treated with lipase from Aspergillus (As) or *Pseudomonas* (Ps) at the indicated concentrations for 18 h at 37° C. Lipase-treated or untreated BP1569 (100 ng/ml) was used to stimulate BMDC from C3H/HeJ mice.

Blocking antibodies were used against TLR2 to determine if the proteins can activate TLR2 specifically. BP1569-induced TNF-α production from DC C3H/HeJ was completely abrogated in the presence of the TLR2 blocking antibody (FIG. 2D). Lipase treatment was used to confirm that the immunostimulatry effects of BP1569 were due the presence of the characteristic acyl side chain of the lipoprotein. The recombinant lipoprotein was incubated with two separate lipases for 18 h prior to stimulation of DC. Lipase treatment abolished BP1569-induced IL-12p40 and IL-6 production (FIG. 2E), but had no effect on cytokine production induced by the TLR9 agonist CpG (data not shown), confirming that BP1569 contains lipid side chains capable of triggering TLR2-induced inflammatory cytokine production. These data demonstrate that BP1569 is a lipoprotein agonist for TLR2 and activates maturation and inflammatory cytokine production by murine DC.

Example 3

BP1569 Activates NF-κB and MAP Kinase Pathways Downstream of TLR2

Figures 3A, 3B, 3C, 3D:
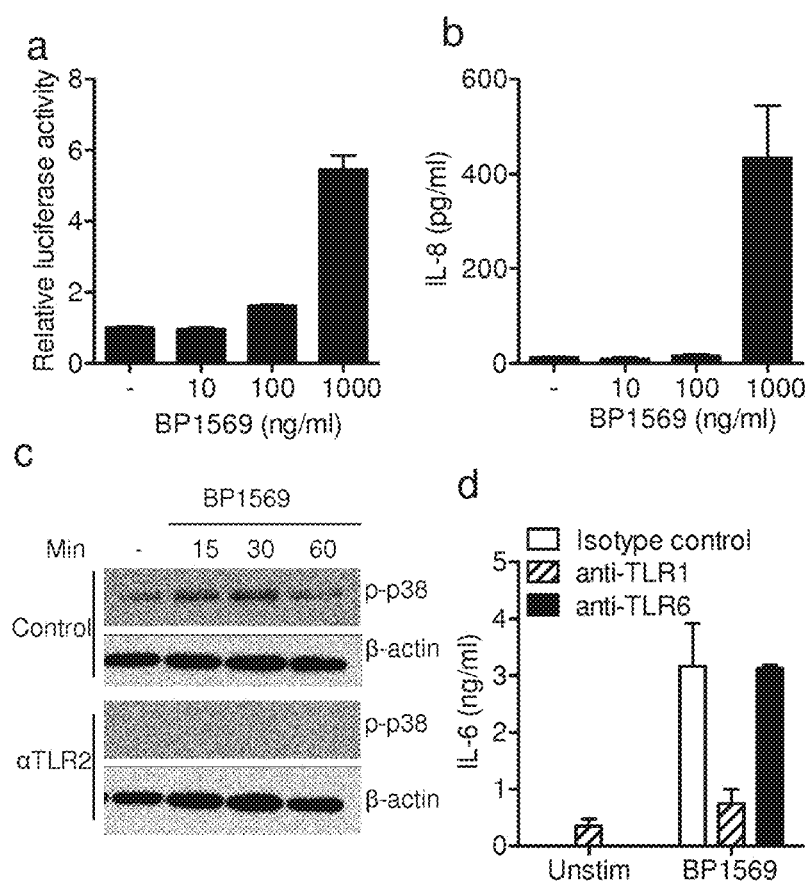
FIGS. 3A-3D demonstrate the activation of NF-κB and MAP kinase pathways by BP1569.

Cytokine production by TLR2 requires activation of the transcription factors NF-κB and p38 MAP kinase. To determine if BP1569 activates NF-κB, HEK 293T cells stably expressing TLR2, but devoid of TLR4, were transfected with an NF-κB luciferase reporter construct. Stimulation of these cells with BP1569 (100 ng/ml) resulted in a significant increase in luciferase activity (FIG. 3A). IL-8 production by TLR2 transfected HEK 293T cells was also increased following stimulation with BP1569, linking activation of the NF-κB pathway with cytokine production (FIG. 3B). To assess activation of the MAP kinase pathway, spleen cells from C3H/HeJ mice were stimulated with BP1569. This treatment enhanced p38 phosphorylation 15 minutes following stimulation, which was inhibited by addition of anti-TLR2 blocking antibody (FIG. 3C). These results demonstrate that BP1569 induces TLR2-dependent activation of NF-κB and p38, two pathways shown to be required for TLR2-induced cytokine production. TLR agonists can bind to TLR1/2 or TLR2/6 heterodimers, therefore, the role of these TLRs using specific blocking antibodies to human TLR1 and TLR6 was examined. Incubation of human PBMC with a TLR1 blocking antibody significantly reduced BP1569-induced IL-6 production, whereas an anti-TLR6 antibody had little effect, suggesting that BP1569 is triacylated rather than diacylated (FIG. 3D).

Example 4

BP1569 Induces Innate Inflammatory Cytokines and is Immunogenic In Vivo

Having demonstrated that BP1569 is capable of activating TLR2 in vitro, whether or not the lipoprotein can induce pro-inflammatory cytokine responses in vivo was determined.

C3H/HeJ mice were treated intraperitoneally with BP1569 (70 µg) and serum cytokines were measured after 3 h. Significant concentrations of IL-6 and IL-12 were detected in the serum of mice treated with the BP1569 versus PBS controls (FIG. 3A).

The possibility that BP1569 was immunogenic in vivo and capable of inducing *B. pertussis*-specific immune responses was examined. C3H/HeJ mice were injected into the footpad with BP1569 (10 µg) diluted in PBS or with PBS only. After seven days the draining lymph node was harvested and the lymph node cells were stimulated with either BP1569 (2 µg/ml) or heat killed *B. pertussis*. BP1569-specific IFN-γ was induced at significant levels in mice immunized with BP1569 but not in mice immunized with PBS (FIG. 3B). Furthermore, cells from immunized mice produced IFN-γ upon re-stimulation with heat killed *B.*

*pertussis*, thus providing evidence that BP1569 is an antigenic component of the bacteria (FIG. 3C).

Example 5

Synthetic Lipopeptide LP1569 Induces Inflammatory Cytokines by Human and Murine Innate Immune Cells The above results demonstrate that BP1569 has immunomodulatory as well as antigenic properties and the former is due to its ability to activate TLR2. In order to provide evidence of TLR2-mediated immunomodulatory activity, and to examine the adjuvant properties of the *B. pertussis* lipoproteins in vivo in conventional mice, a synthetic lipopeptide version of BP1569 was generated. The lipopeptide, named LP1569 to distinguish it from the full length protein, has the conserved cysteine residue palmitylated and followed by 11 amino acids of the protein sequence of BP1569. This represents the mature N-terminus of the lipoprotein following removal of the signal peptide during biosynthesis.

It was first demonstrated that this lipopeptide specifically activates TLR2 by stimulating murine DC with LP1569 in the presence and absence of a TLR2 blocking antibody. LP1569 induced TNF-α production, which was blocked by anti-TLR2 (FIG. 5A). Furthermore, LP1569 induced robust expression of TNF-α, IL-10 and IL-6 by murine macrophages (FIG. 5B). LP1569 also stimulated TNFα production by human PBMC (FIG. 5C). Finally, it was demonstrated that LP1569 induced pro-inflammatory cytokine production in vivo. Injection of mice with LP1569 resulted in a significant enhancement of serum concentrations of IL-12 and IL-6 over that observed in mice injected with PBS (FIG. 5D). These findings demonstrate that the synthetic peptide LP1569 is a TLR2 agonist and activates innate immune responses in vitro and in vivo.

Example 6

LP1569 Enhances Activation of T Cells

The present inventors have shown that BP1569 and LP1569 promote inflammatory cytokine production by DCs, including IL-12, IL-6, and IL-23 that promote the induction or expansion of Th1 and Th17 cells.

Stimulation of spleen cells with LP1569 induced the production of IFN-γ detected by ELISA, which was inhibited upon co-incubation with and anti-IL-12p40 but not an anti-p19 antibody, indicating a role for LP1569 driven IL-12p70 in IFN-γ production (FIG. 6A). Furthermore LP1569 induced IL-17 production by spleen cells following addition of exogenous IL-23 (FIG. 6B). Intracellular cytokine staining and FACS analysis revealed that $CD4^+$ and $CD8^+$ T cells produce IFN-γ following stimulation of the spleen cells with LP1569, which was slightly augmented by addition of IL-1β (FIG. 6C and FIG. 6D). Furthermore, intracellular cytokine staining showed that the combination of LP1569 and IL-23, but LP12569 or IL-23 alone, induced a clear population of IL-17-secreting γδ T cells (FIG. 6E).

Example 7

LP1569 is an Effective Adjuvant for Promoting Protective Cellular Immunity Against *B. pertussis*

Having shown that LP1569 has immunostimulatory activity, promoting innate cytokines that drive T cell responses, the present inventors assessed its adjuvant activity in vivo using protective antigens from *B. pertussis* and established respiratory infection model. The inventors' previous studies using this model have demonstrated a critical role for Th1 and Th17 cells in natural and vaccine-induced immunity to *B. pertussis* (Ross P J et al). Mice were immunized with the *B. pertussis* antigens, FHA, PTd and pertactin alone or with LP1569 or with PBS only and boosted 4 weeks later. Mice were challenged by aerosol exposure to live *B. pertussis* 2 weeks after the second immunization. Assessment of CFU counts in the lungs revealed that immunization with *B. pertussis* antigens without an adjuvant conferred limited protection against *B. pertussis* challenge (FIG. 6A). In contrast, immunization with the experimental acellular pertussis vaccines (Pa) formulated with LP1569 conferred a high level of protection against *B. pertussis*; bacteria were undetectable in immunized mice 3, 7 and 10 days after challenge (FIG. 7A).

Antibody and T cell responses specific for one of the *B. pertussis* antigens, FHA, in immunized mice on the day of challenge were assessed. Immunization with *B. pertussis* antigens alone induced weak FHA-specific serum IgG1 and undetectable IgG2a. In contrast, immunization with *B. pertussis* antigens in combination with LP1569 generate high FHA-specific IgG2a titres in serum (FIG. 7B). Furthermore, the experimental acellular pertussis vaccines (Pa) with LP1569 generated potent Th1 and Th17 responses, with high concentrations of IFN-γ and IL-17 detected in supernatants of FHA-stimulated spleen cells from immunized mice (FIG. 7C). In contrast, immunization with the *B. pertussis* antigens in the absence of the lipopetide generated Th2 type responses, with high IL-5, but substantially lower concentrations of IL-17 and IFN-γ than that generated with the experimental vaccine formulated with LP1569. These findings demonstrate that LP1569 is a potent adjuvant for induction of Th1/Th17 type responses and protection against *B. pertussis*.

Example 8

Therapeutic Administration of LP1569 Slows Tumour Growth and Enhances Survival

The present inventors demonstrated how therapeutic administration of LP1569 slows tumour growth and enhances survival of mice challenged with CT26 colon carcinoma cells. Mice were injected subcutaneously (s.c.) with CT26 colon carcinoma cells and then treated on days 3, 10 and 17 with LP1569 or vehicle only. The data show that the rate of tumor growth is slower in mice treated with LP1569. Furthermore, the survival of tumor-bearing mice is enhanced following treatment with LP1569. These data demonstrated that LP1569 has anti-tumour properties, most likely due to induction of innate and adaptive immune responses against the tumor. Furthermore, this could be enhanced by blocking the anti-inflammatory or regulatory responses also induced with the TLR2 agonists, using inhibitors of Pi3 kinase or p38 MAP kinase or immune checkpoint inhibitors e.g anti-Cytotoxic T-Lymphocyte Antigen 4 (CTLA4) or anti-Programme Death 1 (PD1)/Programmed Death Ligand-1 (PDL1).

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

REFERENCES

Dillon et al (2006) Yeast zymosan, a stimulus for TLR2 and dectin-1, induces regulatory antigen-presenting cells and immunological tolerance. *J Clin Invest;* 116(4): 916-28.

Dunne A, et al. (2010) Inflammasome activation by adenylate cyclase toxin directs Th17 responses and protection against *Bordetella pertussis. J Immunol* 185 (3) : 1711-1719.

Higgs R, Higgins S C, Ross P J, & Mills K H (2012) Immunity to the respiratory pathogen*Bordetella pertussis. Mucosal Immunol* 5(5): 485-500.

Higgins S C, et al. (2003) Toll-like receptor 4-mediated innate IL-10 activates antigen-specific regulatory T cells and confers resistance to *Bordetella pertussis* by inhibiting inflammatory pathology. *J Immunol* 171(6): 3119-3127.

Ross P J, et al. (2013) Relative contribution of Th1 and Th17 cells in adaptive immunity to *Bordetella pertussis*: towards the rational design of an improved acellular pertussis vaccine. *PLoS Pathog* 9(4): e1003264.

Sutherland et al. (2011) Antibodies Recognizing Protective Pertussis Toxin Epitopes Are Preferentially Elicited by Natural Infection versus Acellular Immunization *Clin Vaccine Immunol;* 18(6): 954-962.

The invention claimed is:

1. A method for enhancing a Th1 and Th17 response in a subject in need thereof comprising:
   administering to the subject a lipoprotein obtainable from *Bordetella pertussis*, wherein the lipoprotein comprises an N terminal signal peptide of less than 40 amino acids in length;
   wherein the N terminal signal peptide comprises a lipobox comprising an amino acid sequence X1, X2, X3, and X4;
   wherein X1 is selected from the group consisting of Leucine, Valine and Isoleucine X2 is selected from the group consisting of Alanine, Serine, Threonine, Valine and Isoleucine X3 is selected from the group consisting of Glycine, Alanine, and Serine and X4 is Cysteine;
   wherein X4 is capable of being acylated:
   wherein the lipoprotein is a Toll-like receptor 2 agonist and an adjuvant; and
   enhancing the Th1 and Th17 response, by the lipoprotein, in the subject, wherein the lipoprotein comprises the amino acid sequence of SEQ ID NO:13.

2. The method as claimed in claim 1, wherein the method is a method of treatment or prevention of a condition caused by *B. pertussis*.

3. The method as claimed in 2, wherein the method is a method of vaccinating the subject to induce immunity against *B. pertussis*.

4. The method as claimed in claim 2, wherein the method further comprises administering to the subject an antigen from *B. pertussis*.

* * * * *

SEQUENCE LISTING

```
<160> NUMBER OF SEQ ID NOS: 14

<210> SEQ ID NO 1
<211> LENGTH: 375
<212> TYPE: PRT
<213> ORGANISM: Bordetella pertussis

<400> SEQUENCE: 1

Met Arg Met Asn Lys Arg His Ala Gly Ala Ser Ala Leu Met Ala Leu
1               5                   10                  15

Ala Leu Leu Ala Gly Cys Ser Asp Val Asn Gln Leu Leu Gly Asn Glu
            20                  25                  30

Glu Ser Val Asp Tyr Lys Ser Thr Arg Arg Gly Asp Pro Leu Ser Ile
        35                  40                  45

Pro Pro Asp Leu Thr Gln Ala Asn Asn Asp Pro Arg Tyr Lys Ala Pro
    50                  55                  60

Ala Ser Gly Thr Ala Thr Tyr Ser Gln Phe Gln Gln Gln Gly Leu Gln
65                  70                  75                  80

Gln Gln Ala Ser Ala Gly Gln Asn Thr Asn Val Leu Pro Glu Arg Ala
            85                  90                  95

Asp Met Arg Val Glu Arg Asp Gly Asp Leu Arg Trp Leu Val Ile Glu
            100                 105                 110

Arg Pro Pro Glu Gln Leu Phe Ser Lys Val Val Asp Phe Trp Thr Asp
        115                 120                 125

Thr Gly Phe Thr Val Ser Val Asn Asn Pro Gln Ala Gly Ile Ile Glu
    130                 135                 140

Thr Asp Trp Ala Glu Asn Arg Ala Lys Ile Pro Glu Ser Trp Leu Arg
145                 150                 155                 160

Gln Val Leu Gly Ser Val Leu Glu Thr Ala Trp Asp Ser Gly Glu Arg
            165                 170                 175

Glu Lys Phe Arg Thr Arg Val Glu Arg Val Asn Gly His Thr Glu Ile
            180                 185                 190

Tyr Ile Thr His Asn Gln Met Leu Glu Lys Arg Val Gly Ser Asp Gly
        195                 200                 205

Gly Gln Val Gln Trp Thr His Gly Lys Glu Asp Pro Gly Leu Asn Ala
    210                 215                 220

Ala Met Leu Ala Arg Leu Met Val Tyr Leu Gly Thr Asp Val Asp Ala
225                 230                 235                 240

Ala Arg Lys Leu Val Ala Gln Ala Glu Ala Ala Pro Gln Ala Pro Lys
            245                 250                 255
```

```
Val Gln Ser Val Arg Ala Glu Gly Ala Met Leu Val Val Asp Glu Ser
            260                 265                 270

Phe Asp Arg Ala Trp Arg Val Gly Val Ala Leu Asp Ser Gly Gly
        275                 280                 285

Phe Ala Val Asp Asp Arg Asp Arg Ser Ala Gly Glu Tyr Phe Val Arg
        290                 295                 300

Tyr Val Asp Thr Asp Thr Gly Ala Gln Asn Glu Gln Pro Gly Phe Phe
305                 310                 315                 320

Ser Arg Leu Phe Ser Ser Asp Lys Lys Ala Gln Ala Pro Gln Tyr Arg
                325                 330                 335

Ile Arg Leu Thr Gly Ser Gly Thr Gln Thr Gln Val Thr Val Leu Asp
                340                 345                 350

Ala Asn Gly Gln Arg Asp Ser Ser Ala Thr Ala Gln Arg Met Leu Ser
                355                 360                 365

Val Leu Lys Asp Lys Met Val
                370             375

<210> SEQ ID NO 2
<211> LENGTH: 166
<212> TYPE: PRT
<213> ORGANISM: Bordetella pertussis

<400> SEQUENCE: 2

Asn Tyr Met His Ser Pro Ser Val Val Ala Gly Arg Ala Arg Leu
1               5                   10                  15

Leu Ala Val Ala Ala Val Ala Gly Ser Val Ala Val Leu Ala Gly Cys
                20                  25                  30

Ala Asn Pro Ser Ala Ser Ser Gly Val Tyr Thr Tyr Gly Gln Ala Gln
                35                  40                  45

Arg Glu Gln Ile Val Arg Thr Gly Thr Val Thr Gly Val Arg Pro Ile
            50                  55                  60

Thr Ile Gln Asn Asp Lys Ser Ser Gly Val Gly Leu Val Ala Gly Gly
65                  70                  75                  80

Ala Leu Gly Gly Val Ala Gly Asn Ala Val Gly Gly Thr Gly Arg
                85                  90                  95

Thr Ile Ala Thr Val Gly Gly Val Ile Leu Gly Ala Leu Ala Gly Asn
                100                 105                 110

Ala Ile Glu Asn Arg Ala Gly Lys Ser Ser Gly Tyr Glu Ile Thr Val
                115                 120                 125

Arg Leu Asp Asn Gly Glu Thr Arg Val Val Ala Gln Glu Ala Asp Val
            130                 135                 140

Pro Ile Ser Val Gly Gln Arg Val Gln Val Ile Ser Gly Ala Gly Pro
145                 150                 155                 160

Thr Arg Val Thr Pro Tyr
                165

<210> SEQ ID NO 3
<211> LENGTH: 188
<212> TYPE: PRT
<213> ORGANISM: Bordetella pertussis

<400> SEQUENCE: 3

Met Gln Leu Thr Ile Arg Lys Leu Ala Tyr Thr Leu Ala Phe Ser Thr
1               5                   10                  15

Leu Val Leu Ala Gly Cys Thr Thr Ala Ser Lys Lys Thr Asp Gly Gln
                20                  25                  30
```

```
Ala Ala Thr Pro Ala Asp Gln Ala Ser Ser Gln Gln Ala Ser Ala Ala
            35                  40                  45

Ser Val Glu Phe Tyr Val Ala Gln Ala Lys Ala Gly Asp Gly Leu Met
 50                  55                  60

Glu Val Lys Val Pro Asp Gly Ser Leu Tyr Met Gln Arg Gln Pro Val
 65                  70                  75                  80

Leu Thr Arg Ala Asp Leu Thr Glu Ala Ala Leu Val Asp Arg Gln
                 85                  90                  95

Gly Gln Asn Phe Val Gly Leu Arg Phe Thr Glu Ala Gly Ala Arg Lys
                100                 105                 110

Leu Asn Asp Ile Ser Ser Lys Asn Ile Gly Asn Met Leu Ala Leu Val
                115                 120                 125

Ile Asp Arg Glu Leu Val Ala Ala Pro Arg Ile Ala Glu Pro Leu Asn
                130                 135                 140

Arg Gly Val Leu Ala Phe Gly Val Pro Ser Ala Lys Ala Ala Ser Glu
145                 150                 155                 160

Ile Ala Ala Lys Ile Arg Gly Asp Ala Gly Pro Ala Ala Gly Val
                165                 170                 175

Pro Ala Ala Pro Ala Pro Lys Pro Ala Pro Lys Pro
                180                 185

<210> SEQ ID NO 4
<211> LENGTH: 165
<212> TYPE: PRT
<213> ORGANISM: Bordetella pertussis

<400> SEQUENCE: 4

Met Lys Ser Arg Ile Ala Lys Ser Leu Thr Ile Ala Ala Leu Ala Ala
 1               5                  10                  15

Thr Leu Ala Ala Cys Ser Ser Val Pro Leu Asp Asp Lys Ala Gly Gln
                20                  25                  30

Ala Gly Gly Ser Gly Gln Gly Ser Ala Ser Gly Gln Ile Leu Asp Pro
                35                  40                  45

Phe Asn Pro Gln Ser Ile Leu Ala Gln Gln Arg Ser Val Tyr Phe Asp
 50                  55                  60

Phe Asp Ser Tyr Thr Val Ser Glu Gln Tyr Arg Gly Leu Val Glu Thr
 65                  70                  75                  80

His Ala Arg Tyr Leu Ala Ser Asn Asn Gln Gln Arg Ile Lys Ile Glu
                 85                  90                  95

Gly Asn Thr Asp Glu Arg Gly Gly Ala Glu Tyr Asn Leu Ala Leu Gly
                100                 105                 110

Gln Arg Arg Ala Asp Ala Val Arg Arg Met Met Thr Leu Leu Gly Val
                115                 120                 125

Ser Asp Asn Gln Ile Glu Thr Ile Ser Phe Gly Lys Glu Lys Pro Lys
                130                 135                 140

Ala Thr Gly Ser Ser Glu Ala Asp Phe Ala Glu Asn Arg Arg Ala Asp
145                 150                 155                 160

Ile Val Tyr Gln Arg
                165

<210> SEQ ID NO 5
<211> LENGTH: 247
<212> TYPE: PRT
<213> ORGANISM: Bordetella pertussis
```

<400> SEQUENCE: 5

Met Ser Ala Pro Leu Asp Thr Pro Ala Leu Arg Leu Asn Thr Arg Phe
1               5                   10                  15

Ala Thr Gly Ile Val Leu Ala Gly Thr Leu Ala Leu Ala Gly Cys Ala
            20                  25                  30

Gln Gln Arg Ser Ala Gly Tyr Tyr Asp Pro Pro Gly Ala Ser Thr Ile
        35                  40                  45

Thr Asp Ala Gln Tyr Gln Gly Gln Ala Ala Gly Tyr Arg Thr Val Val
    50                  55                  60

His Ala Pro Ser Gln Leu Gln Ile Glu Leu Lys Pro Asn Gln Pro Ala
65                  70                  75                  80

Arg Gln Gln Asn Ala Gln Ala Gln Gly Gln Gln Ser Thr Glu Asp
                85                  90                  95

Gly Thr Ala Val Pro Glu Gly Gln Ala Ala Pro Gln Pro Gln Pro Glu
                100                 105                 110

Thr Ala Ser Pro Gly Ala Gln Ala Ile Ile Pro Gln Ala Gln Thr Tyr
                115                 120                 125

Gln Gly Thr Phe Pro Cys Phe Ala Ala Gly Leu Ala Cys Glu Ala Gln
        130                 135                 140

Arg Val Thr Leu Thr Leu Ala Pro Asn Gly Arg Trp Arg Ser Arg Thr
145                 150                 155                 160

Asn Tyr Leu Asp Lys Gln Pro Gln Ala Ser Ala Pro Val Ala Glu Gln
                165                 170                 175

Gly Cys Trp Asp Ala Thr Gln Glu Arg Pro Pro Arg Val Leu Leu Leu
            180                 185                 190

Asp Gly Ser Gly Asn Met Arg Ala Glu Leu Val Met Thr Ala Asn Asn
        195                 200                 205

Val Leu Arg Val Arg Ser Val Gly Gly Arg Thr Pro Asn Leu Asn Tyr
    210                 215                 220

Asn Leu Thr Arg Gln Pro Asp Leu Asp Ala Ile Ala Glu Leu Asp Lys
225                 230                 235                 240

Gln Ala Ala Pro Lys Cys Pro
                245

<210> SEQ ID NO 6
<211> LENGTH: 182
<212> TYPE: PRT
<213> ORGANISM: Bordetella pertussis

<400> SEQUENCE: 6

Met Ile Ala Arg Ile Ser Leu Arg Pro Leu Lys Gly Leu Ala Val Ala
1               5                   10                  15

Val Leu Ala Ala Ser Ala Leu Thr Ala Cys Ser Ser Gly Lys Trp Gly
            20                  25                  30

Phe Pro Tyr Lys Ala Gly Val Gln Gln Gly Asn Trp Ile Thr Lys Glu
        35                  40                  45

Gln Val Ala Leu Leu Gln Gln Gly Met Ser Arg Glu Gln Val Arg Phe
    50                  55                  60

Ala Leu Gly Ser Pro Thr Leu Thr Ser Val Leu His Ala Asp Arg Trp
65                  70                  75                  80

Asp Tyr Pro Tyr Tyr Phe Lys Pro Gly Tyr Gly Lys Ala Gln Glu Arg
                85                  90                  95

Gln Phe Thr Val Trp Phe Glu Asn Asp His Leu Val Arg Trp Ser Gly
            100                 105                 110

```
Asp Glu Gln Pro Asp Leu Gln Pro Phe Gln Ile Glu Lys Val Asn Ala
            115                 120                 125
Lys Gln Glu Glu Lys Ala Asp Ala Gln Val Asp Thr Ala Glu Lys Arg
        130                 135                 140
Gln Glu Gly Ile Asp Lys Ala Glu Lys Val Arg Pro His Val Asp Val
145                 150                 155                 160
Thr Thr Pro Asp Asn Pro Thr Leu Asp Tyr Pro Gly Glu Pro Gly Gln
                165                 170                 175
Thr Phe Glu Pro Leu Lys
            180

<210> SEQ ID NO 7
<211> LENGTH: 22
<212> TYPE: PRT
<213> ORGANISM: Bordetella pertussis

<400> SEQUENCE: 7

Met Arg Met Asn Lys Arg His Ala Gly Ala Ser Ala Leu Met Ala Leu
1               5                   10                  15
Ala Leu Leu Ala Gly Cys
            20

<210> SEQ ID NO 8
<211> LENGTH: 33
<212> TYPE: PRT
<213> ORGANISM: Bordetella pertussis

<400> SEQUENCE: 8

Met Asn Tyr Met His Ser Pro Ser Val Val Ala Gly Arg Ala Arg Arg
1               5                   10                  15
Leu Leu Ala Val Ala Ala Val Ala Gly Ser Val Ala Val Leu Ala Gly
            20                  25                  30
Cys

<210> SEQ ID NO 9
<211> LENGTH: 22
<212> TYPE: PRT
<213> ORGANISM: Bordetella pertussis

<400> SEQUENCE: 9

Met Gln Leu Thr Ile Arg Lys Leu Ala Tyr Thr Leu Ala Phe Ser Thr
1               5                   10                  15
Leu Val Leu Ala Gly Cys
            20

<210> SEQ ID NO 10
<211> LENGTH: 21
<212> TYPE: PRT
<213> ORGANISM: Bordetella pertussis

<400> SEQUENCE: 10

Met Lys Ser Arg Ile Ala Lys Ser Leu Thr Ile Ala Ala Leu Ala Ala
1               5                   10                  15
Thr Leu Ala Ala Cys
            20

<210> SEQ ID NO 11
<211> LENGTH: 31
<212> TYPE: PRT
<213> ORGANISM: Bordetella pertussis
```

```
<400> SEQUENCE: 11

Met Ser Ala Pro Leu Asp Thr Pro Ala Leu Arg Leu Asn Thr Arg Phe
1               5                   10                  15

Ala Thr Gly Ile Val Leu Ala Gly Thr Leu Ala Leu Ala Gly Cys
            20                  25                  30

<210> SEQ ID NO 12
<211> LENGTH: 26
<212> TYPE: PRT
<213> ORGANISM: Bordetella pertussis

<400> SEQUENCE: 12

Met Ile Ala Arg Ile Ser Leu Arg Pro Leu Lys Gly Leu Ala Val Ala
1               5                   10                  15

Val Leu Ala Ala Ser Ala Leu Thr Ala Cys
            20                  25

<210> SEQ ID NO 13
<211> LENGTH: 15
<212> TYPE: PRT
<213> ORGANISM: Bordetella pertussis

<400> SEQUENCE: 13

Cys Ser Asp Val Asn Gln Leu Leu Gly Asn Glu Glu Ser Val Asp
1               5                   10                  15

<210> SEQ ID NO 14
<211> LENGTH: 15
<212> TYPE: PRT
<213> ORGANISM: Bordetella pertussis

<400> SEQUENCE: 14

Cys Ala Asn Pro Ser Ala Ser Ser Gly Val Tyr Thr Tyr Gly Gln
1               5                   10                  15
```